(12) United States Patent
Guevremont et al.

(10) Patent No.: US 6,753,522 B2
(45) Date of Patent: Jun. 22, 2004

(54) FAIMS APPARATUS HAVING PLURAL ION INLETS AND METHOD THEREFORE

(75) Inventors: Roger Guevremont, Ottawa (CA); Randy Purves, Orleans (CA); David Barnett, Orleans (CA)

(73) Assignee: Ionalytics Corporation, Ottawa (CA)

( * ) Notice: Subject to any disclaimer, the term of this patent is extended or adjusted under 35 U.S.C. 154(b) by 0 days.

(21) Appl. No.: 10/359,642

(22) Filed: Feb. 7, 2003

(65) Prior Publication Data

US 2003/0230711 A1 Dec. 18, 2003

Related U.S. Application Data

(60) Provisional application No. 60/354,711, filed on Feb. 8, 2002.

(51) Int. Cl.[7] .............................................. B01D 59/44
(52) U.S. Cl. ........................ 250/287; 250/283; 250/286; 250/281; 250/282; 250/292
(58) Field of Search .................................. 250/290, 292, 250/283, 281, 282, 286, 287, 288, 285

(56) References Cited

U.S. PATENT DOCUMENTS

| | | | |
|---|---|---|---|
| 5,420,424 A | | 5/1995 | Carnahan et al. |
| 5,905,258 A | | 5/1999 | Clemmer et al. |
| 6,124,592 A | * | 9/2000 | Spangler ..................... 250/287 |
| 6,621,077 B1 | * | 9/2003 | Guevremont et al. ....... 250/292 |
| 6,639,212 B1 | * | 10/2003 | Guevremont et al. ....... 250/282 |

FOREIGN PATENT DOCUMENTS

| | | |
|---|---|---|
| DE | 197 30 896 A1 | 1/1999 |
| WO | WO 00/08455 A1 | 2/2000 |
| WO | WO 00/63949 A1 | 10/2000 |
| WO | WO 01/44795 A2 | 6/2001 |
| WO | WO 01/69217 A2 | 9/2001 |
| WO | WO 01/69221 A2 | 9/2001 |

OTHER PUBLICATIONS

Carr et al., "Plasma Chromatography", Plenum Press (1984), NY, USA.

Mason et al., "Transport Properties of Ions in Gases", Wiley (1988), NY USA.

(List continued on next page.)

*Primary Examiner*—Jack Berman
*Assistant Examiner*—Johnnie L. Smith, II
(74) *Attorney, Agent, or Firm*—Freedman & Associates

(57) ABSTRACT

Disclosed are an apparatus and a method for separating ions in the gas phase. An apparatus according to the instant invention includes a high field asymmetric waveform ion mobility spectrometer including an inner electrode having an outer surface and a length. The apparatus further includes an outer electrode having an inner surface and a length and surrounding the inner electrode over at least a portion of the length of the inner electrode, the inner electrode and the outer electrode defining an analyzer region therebetween and being disposed in a spaced apart arrangement for allowing ions to propagate therebetween. The outer electrode also includes an outlet from the analyzer region and at least a first ion inlet and a second distinct ion inlet into the analyzer region. The first ion inlet and the second distinct ion inlet are each for communicating with at least one ionization source. The inner electrode and the outer electrode are for providing an electric field within the analyzer region resulting from application of an asymmetric waveform voltage to at least one of the inner electrode and the outer electrode and from application of a compensation voltage to at least one of the inner electrode and outer electrode, the electric field for selectively transmitting ions within the analyzer region between at least one of the first ion inlet and the second distinct ion inlet and the outlet.

42 Claims, 20 Drawing Sheets

OTHER PUBLICATIONS

Buryakov et al., "A New Method of Separation of Multi–Atomic Ions by Mobility at Atmospheric Pressure using a High–Frequency Ampliturd–Asymmetric Strong Electric Field", Int. J. Mass Spectrom. Ion Processes, No. 128, pp. 143–148, Elsevier Science Publishers B.V. (1993).

Eiceman et al., "Ion Mobility Spectrometry", (1994), CRC Press, FL, USA.

Carnahan et al., "Field Ion Spectrometry —A New Analytical Technology for Trace Gas Analysis", Proceedings of the 41st Annual ISA Analysis Division Symposium, paper #96–009, pp. 87–95, (1996), Framingham, MA, USA.

Riegner et al., "Qualitative Evaluation of Field Ion Spectrometry for Chemical Warfare Agent Detection", Proceedings of the 45th ASMS Conference on Mass Spectrometry and Allied Topics, pp. 473, (1997), Palm Springs, CA, USA.

Krylov, "A Method of Reducing Diffusion Losses in a Drift Spectrometer", Tech. Phys., vol. 44, No. 1, pp. 113–116, American Institute of Physics (1999).

Spangler, "Fundamental Considerations for the Application of Miniature Ion Mobility Spectrometry to Field Analytical Applications ", Field Analytic Chemistry and Technology, 4, pp. 255–267 (2000), USA.

Eiceman et al., "Monitoring Volatile Organic Compounds in Ambient Air Anside and Outside Buildings with the use of a Radio–Frequency–Based Ion–Mobility Analyzer with a Micromachined Drift Tube", Field Analytical Chemistry and Technology, 4, pp. 297–308 (2000), USA.

Miller et al., "A Novel Micromachined High–Field Asymmetric Waveform–Ion Mobility Spectrometer", Sensors and Actuators B Chemical, 37, pp. 300–306, Elsevier Science S.A. (2000).

Miller et al., "A MEMS Radio–Frequency Ion Mobility Spectrometer for Chemical Vapor Detection", Sensors and Actuators A Physical, 91, pp. 307–318, Elsevier Science S.A. (2000).

Eiceman et al., "Miniature Radio–Frequency Mobility Analyzer as a Gas Chromatographic Detector for Oxygen–Containing Volatile Organic Compounds, Phermonoes and other insect Attractants", Journal of Chromatography A, 917, pp. 205–217, Elsevier Science B.V. (2001).

Buryakov et al., "Detection of Explosive Vapors in the Air Using an Ion Drift Nonlinearity Spectrometer", Journal of Analytic Chemistry , vol. 56, No. 4, pp. 336–340 (2001).

Guevremont et al., "Atmospheric Pressure Ion Trapping in a Tandem FAIMS–FAIMS Coupled to a TOFMS: Studies with Electrospray Generated Gramicidin S ions", Journal of the American Society for Mass Spectrometry, vol. 12, pp. 1320–1330, Elsevier Science Inc. (2001).

Spangler et al., "Application of Mobility Theory to the Interpretation of Data Generated by Linear and RF Excited Ion Mobility Spectrometers", International Journal of Mass Spectrometry, 12017, pp. 1–10, Elsevier Science B.V. (2002).

* cited by examiner

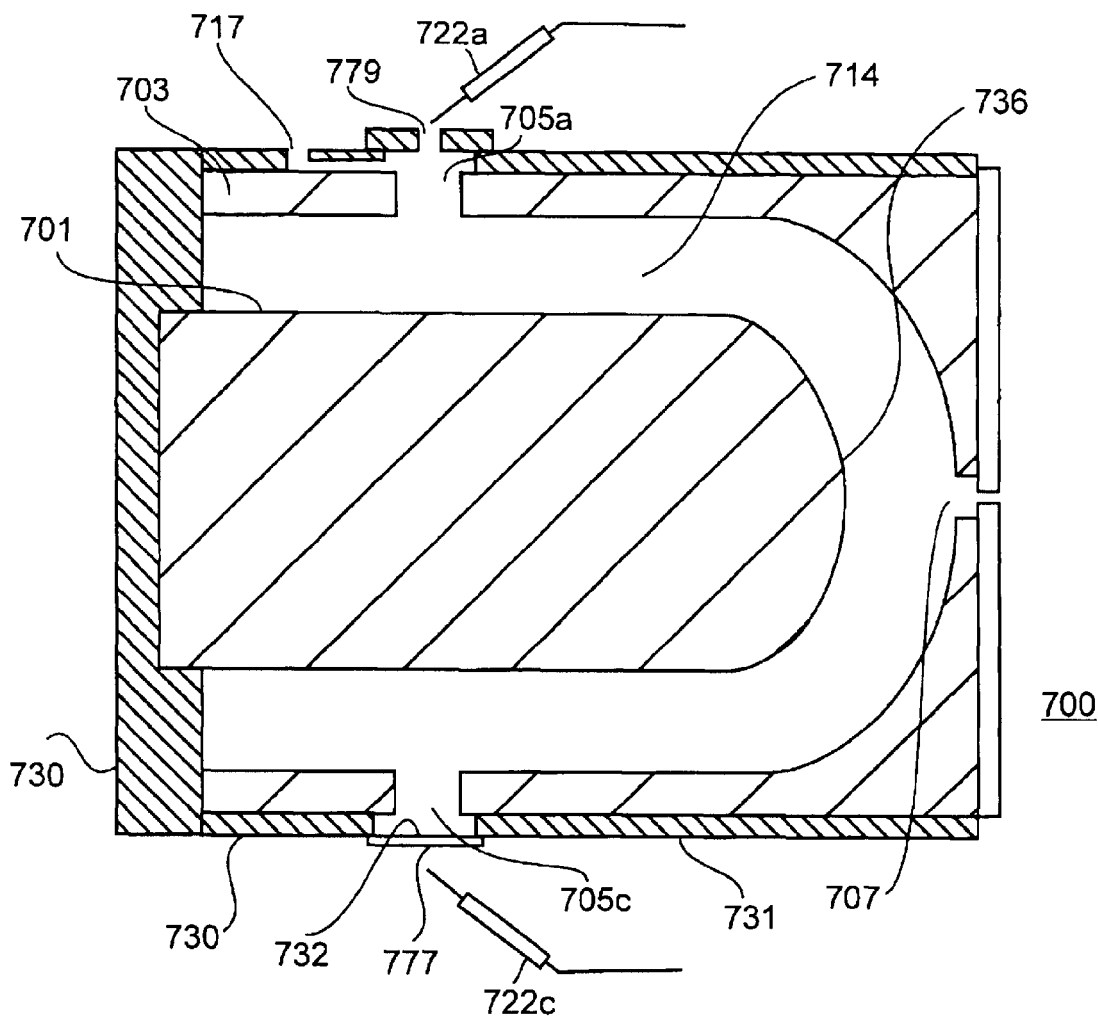
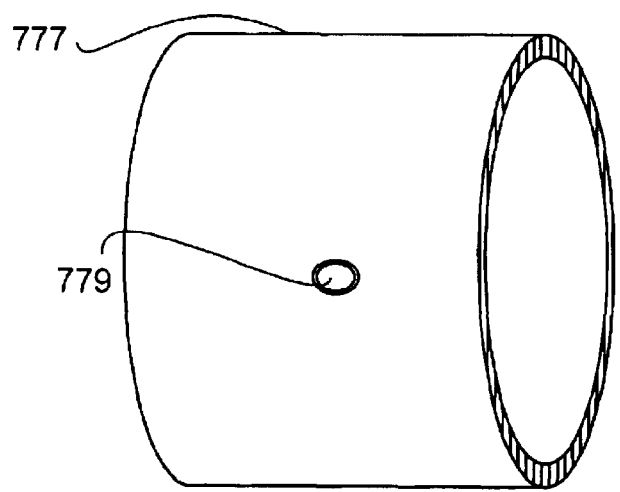
Figure 7a
Figure 7b

FAIMS APPARATUS HAVING PLURAL ION INLETS AND METHOD THEREFORE

This application claims the benefit of U.S. Provisional Application No. 60/354,711 filed Feb. 8, 2002.

FIELD OF THE INVENTION

The instant invention relates generally to high field asymmetric waveform ion mobility spectrometry (FAIMS), more particularly the instant invention relates to FAIMS device having an inner electrode and an outer electrode, in which are disposed multiple inlets for gases and ion streams.

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994). In IMS, gas-phase ion mobilities are determined using a drift tube with a constant electric field. Ions are separated in the drift tube on the basis of differences in their drift velocities. At low electric field strength, for example 200 V/cm, the drift velocity of an ion is proportional to the applied electric field strength, and the mobility, K, which is determined from experimentation, is independent of the applied electric field. Additionally, in IMS the ions travel through a bath gas that is at sufficiently high pressure that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, New York, 1988) teach that at high electric field strength, for instance fields stronger than approximately 5,000 V/cm, the ion drift velocity is no longer directly proportional to the applied electric field, and K is better represented by $K_H$, a non-constant high field mobility term. The dependence of $K_H$ on the applied electric field has been the basis for the development of high field asymmetric waveform ion mobility spectrometry (FAIMS). Ions are separated in a FAIMS analyzer on the basis of a difference in the mobility of an ion at high field strength, $K_H$, relative to the mobility of the ion at low field strength, K. In other words, the ions are separated due to the compound dependent behavior of $K_H$ as a function of the applied electric field strength.

In general, a device for separating ions according to the FAIMS principle has an analyzer region that is defined by a space between first and second spaced-apart electrodes. The first electrode is maintained at a selected dc voltage, often at ground potential, while the second electrode has an asymmetric waveform V(t) applied to it. The asymmetric waveform V(t) is composed of a repeating pattern including a high voltage component, $V_H$, lasting for a short period of time $t_H$ and a lower voltage component, $V_L$, of opposite polarity, lasting a longer period of time $t_L$. The waveform is synthesized such that the integrated voltage-time product, and thus the field-time product, applied to the second electrode during each complete cycle of the waveform is zero, for instance $V_H t_H + V_L t_L = 0$; for example +2000 V for 10 μs followed by −1000 V for 20 μs. The peak voltage during the shorter, high voltage portion of the waveform is called the "dispersion voltage" or DV, which is identically referred to as the applied asymmetric waveform.

Generally, the ions that are to be separated are entrained in a stream of gas flowing through the FAIMS analyzer region, for example between a pair of horizontally oriented, spaced-apart electrodes. Accordingly, the net motion of an ion within the analyzer region is the sum of a horizontal x-axis component due to the stream of gas and a transverse y-axis component due to the applied electric field. During the high voltage portion of the waveform an ion moves with a y-axis velocity component given by $V_H = K_H E_H$, where $E_H$ is the applied field, and $K_H$ is the high field ion mobility under operating electric field, pressure and temperature conditions. The distance traveled by the ion during the high voltage portion of the waveform is given by $d_H = v_H t_H = K_H E_H t_H$, where $t_H$ is the time period of the applied high voltage. During the longer duration, opposite polarity, low voltage portion of the asymmetric waveform, the y-axis velocity component of the ion is $v_L = KE_L$, where K is the low field ion mobility under operating pressure and temperature conditions. The distance traveled is $d_L = v_L t_L = KE_L t_L$. Since the asymmetric waveform ensures that $(V_H t_H) + (V_L t_L) = 0$, the field-time products $E_H t_H$ and $E_L t_L$ are equal in magnitude. Thus, if $K_H$ and K are identical, $d_H$ and $d_L$ are equal, and the ion is returned to its original position along the y-axis during the negative cycle of the waveform. If at $E_H$ the mobility $K_H > K$, the ion experiences a net displacement from its original position relative to the y-axis. For example, if a positive ion travels farther during the positive portion of the waveform, for instance $d_H > d_L$, then the ion migrates away from the second electrode and eventually will be neutralized at the first electrode.

In order to reverse the transverse drift of the positive ion in the above example, a constant negative dc voltage is applied to the second electrode. The difference between the dc voltage that is applied to the first electrode and the dc voltage that is applied to the second electrode is called the "compensation voltage" (CV). The CV voltage prevents the ion from migrating toward either the second or the first electrode. If ions derived from two compounds respond differently to the applied high strength electric fields, the ratio of $K_H$ to K may be different for each compound. Consequently, the magnitude of the CV that is necessary to prevent the drift of the ion toward either electrode is also different for each compound. Thus, when a mixture including several species of ions, each with a unique $K_H/K$ ratio, is being analyzed by FAIMS, only one species of ion is selectively transmitted to a detector for a given combination of CV and DV. In one type of FAIMS experiment, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained.

Guevremont et al. have described the use of curved electrode bodies, for instance inner and outer cylindrical electrodes, for producing a two-dimensional atmospheric pressure ion focusing effect that results in higher ion transmission efficiencies than can be obtained using, for example, a FAIMS device having parallel plate electrodes. In particular, with the application of an appropriate combination of DV and CV an ion of interest is focused into a band-like region in the annular gap between the cylindrical electrodes as a result of the electric fields, which change with radial distance. Focusing the ions of interest has the effect of reducing the number of ions of interest that are lost as a result of the ion suffering a collision with one of the inner and outer electrodes. FAIMS devices with cylindrical electrode geometry have been described in the prior art, as for example in U.S. Pat. No. 5,420,424, the contents of which are incorporated herein by reference.

In WO 00/08455, the contents of which are incorporated herein by reference, Guevremont and Purves describe a domed-FAIMS analyzer. In particular, the domed-FAIMS analyzer includes a cylindrical inner electrode having a curved surface terminus proximate an ion outlet orifice of the FAIMS analyzer region. The curved surface terminus is substantially continuous with the cylindrical shape of the inner electrode and is aligned co-axially with the ion outlet orifice. During use, the application of an asymmetric waveform to the inner electrode results in the normal ion-focusing behavior as described above, and in addition the ion-focusing action extends around the generally spherically shaped terminus of the inner electrode. This causes the selectively transmitted ions to be directed generally radially inwardly within the region that is proximate the terminus of the inner electrode. Several contradictory forces are acting on the ions in this region near the terminus of the inner electrode. The force of the carrier gas flow tends to influence the ions to travel towards the ion-outlet orifice, which advantageously also prevents the ions from migrating in a reverse direction, back towards the ion source. Additionally, the ions that get too close to the inner electrode are pushed back away from the inner electrode, and those near the outer electrode migrate back towards the inner electrode, due to the focusing action of the applied electric fields. When all forces acting upon the ions are balanced, the ions are effectively captured in every direction, either by forces of the flowing gas, or by the focusing effect of the electric fields of the FAIMS mechanism. This is an example of a three-dimensional atmospheric pressure ion trap, as described in greater detail by Guevremont and Purves in WO 00/08457, the contents of which are incorporated herein by reference.

Guevremont and Purves further disclose a near-trapping mode of operation for the above-mentioned domed-FAIMS analyzer, which achieves ion transmission from the domed-FAIMS to a mass spectrometer with high efficiency. Under near-trapping conditions, the ions that accumulate in the three-dimensional region of space near the spherical terminus of the inner electrode are caused to leak from this region, being pulled by a flow of gas towards the ion-outlet orifice. The ions that are extracted from this region do so as a narrow, approximately collimated beam, which is pulled by the gas flow through the ion-outlet orifice and into a small orifice leading into the vacuum system of the mass spectrometer. Accordingly, a tandem domed-FAIMS/MS device is a highly sensitive instrument that is capable of detecting and identifying ions of interest at part-per-billion levels.

More recently, in WO 01/69216 the contents of which is incorporated herein by reference, Guevremont and Purves describe a so-called "perpendicular-gas-flow-FAIMS", which is identically referred to as a side-to-side FAIMS. The analyzer region of the side-to-side FAIMS is defined by an annular space between inner and outer cylindrical electrodes. In particular, ions that are introduced into the analyzer region of the side-to-side FAIMS are selectively transmitted in a direction that is generally around the circumference of the inner electrode. For instance, the ion inlet and the ion outlet of a side-to-side FAIMS device are disposed, one opposing the other, within a surface of the outer electrode such that ions are selectively transmitted through the curved analyzer region between the ion inlet and the ion outlet along a continuously curving ion flow path absent a portion having a substantially linear component. In particular, the ions travel from the ion inlet to the ion outlet by flowing around the inner electrode in one of a "clockwise" and a "counter clock-wise" direction. This is in contrast to the above-mentioned FAIMS devices in which the ions are selectively transmitted along the length of the inner electrode.

Advantageously, the side-to-side FAIMS device reduces the minimum distance that must be traveled by the ions within the analyzer region to approximately fifty percent of the circumference of the inner electrode. Since the ions split into two streams traveling in opposite directions around the inner electrode after they are introduced through the ion inlet, the effective ion density within the analyzer region is reduced, and so too is the ion-ion repulsion space charge effect reduced. Furthermore, the reduction of the minimum ion travel distance has the added benefit of improving the ion transmission efficiency. For example, by keeping the time for travel short, the effect of diffusion and ion-ion repulsion forces are minimized. In keeping distances short, the transit time of the ions through the analyzer region is also short, which supports more rapid analysis of ion mixtures.

Of course, there are various drawbacks associated with state of the art side-to-side FAIMS devices, particularly relating to an efficient utilization of a FAIMS analyzer. The down time of a FAIMS analyzer is often determined not by limitations of the FAIMS device itself, but by specifics of an ion source, or by requirements due to sample preparation. It would be highly advantageous to provide an apparatus which overcomes this problem of the prior art. A FAIMS device in communication with a plurality of ion sources, allows for a more efficient utilization of the FAIMS analyzer. Also, each ion source of the plurality of ion sources could be an embodiment of a different ionization technique. This would provide for an advanced method for optimizing ionization conditions for an unknown sample. Also, Tandem-FAIMS devices comprising two FAIMS analyzers are known in the prior art; however, while ions are accumulated in one trapping FAIMS analyzer before being released to the second one, the second continuous FAIMS analyzer is idling, and is not used. Advantageously, in a Tandem FAIMS application, the continuous FAIMS analyzer is in communication with a plurality of trapping FAIMS analyzers, and is utilized to its fullest extent.

It would be advantageous to provide a simple concept, which allows for the construction of a FAIMS device that overcomes the drawbacks of the prior art.

SUMMARY OF THE INVENTION

In accordance with an aspect of the instant invention there is provided an apparatus for separating ions in the gas phase, comprising: a high field asymmetric waveform ion mobility spectrometer including an inner electrode having an outer surface and a length; and, an outer electrode having an inner surface and a length and surrounding the inner electrode over at least a portion of the length of the inner electrode, the inner electrode and the outer electrode defining an analyzer region therebetween and being disposed in a spaced apart arrangement for allowing ions to propagate therebetween, the outer electrode comprising an outlet from the analyzer region and at least a first ion inlet and a second distinct ion inlet into the analyzer region, the first ion inlet and the second distinct ion inlet each for communicating with at least one ionization source, the inner electrode and the outer electrode for providing an electric field within the analyzer region resulting from application of an asymmetric waveform voltage to at least one of the inner electrode and the outer electrode and from application of a compensation voltage to at least one of the inner electrode and outer electrode, the electric field for selectively transmitting ions within the analyzer region between at least one of the first ion inlet and the second distinct ion inlet and the outlet.

In accordance with another aspect of the instant invention there is provided method for separating ions originating from different ion sources, the method comprising the steps of: providing a high field asymmetric waveform ion mobility spectrometer having at least a first ion inlet and a second distinct ion inlet into an analyzer region thereof, the at least a first ion inlet and a second distinct ion inlet being separately in fluid communication with a first ionization source and a second ionization source, respectively; directing ions from at least one of the first ionization source and the second ionization source toward the first ion inlet and the second distinct ion inlet, respectively; receiving ions including ions of interest into the analyzer region via at least one of the first ion inlet and the second ion inlet; and, transmitting the ions of interest through the analyzer region between the at least one of the first ion inlet and the second distinct ion inlet and an outlet of the analyzer region.

BRIEF DESCRIPTION OF THE DRAWINGS

Exemplary embodiments of the invention will now be described in conjunction with the following drawings, in which similar reference numerals designate similar items:

FIG. 1b is a side elevational view of the cylindrical side-to-side FAIMS device shown in FIG. 1a;

FIG. 7a shows a cross sectional side view of a FAIMS device including an ionization source selecting electrode;

FIG. 7b shows a side view of the ionization source selecting electrode in the form of a rotating ring having an opening;

FIG. 7d shows a cross sectional end view of the FAIMS device of FIG. 7a;

FIG. 9a shows a time-profile of the $V_{tF1}$ voltage applied to the inner electrode of one of the trapping FAIMS devices of the multiple FAIMS device of FIG. 8a;

FIG. 9b shows a time-profile of the $V_{tF2}$ voltage applied to the inner electrode the other one of the trapping FAIMS devices of the multiple FAIMS device of FIG. 8a;

FIG. 9c shows a time-profile for the CV applied to the inner electrode of the other FAIMS device of the multiple FAIMS device of FIG. 8a;

DETAILED DESCRIPTION OF THE INVENTION

The following description is presented to enable a person skilled in the art to make and use the invention, and is provided in the context of particular applications thereof. Various modifications of the disclosed embodiments will be apparent to those of skill in the art, and the general principles defined herein are readily applied to other embodiments and applications without departing from the spirit and scope of the invention. Thus, the present invention is not intended to be limited to the embodiments disclosed, but is to be accorded the widest scope consistent with the principles and features disclosed herein.

The underlying principle that the disclosed embodiments have in common is the presence of a plurality of ion inlets provided through a FAIMS electrode into an analyzer region of a FAIMS device, the ion inlets for communicating with one or more ionization source. The term ionization source is intended to include any device that produces ions of a temporary nature in a dynamic fashion. Some non-limiting examples of ionization sources that are envisaged for use with the instant invention include: an electrospray ionization source, a corona discharge ionization source, a radioactive foil ionization source, a photoionization source, a laser source, etc. In the detailed description and in the claims that follow, an ion inlet is considered to be communicating with an ionization source when there is a reasonable probability that an ion of interest, which is flowing along an ion flow route from the ionization source to the ion inlet, will pass through the ion inlet and enter into the analyzer region. Optionally, a portion of the ion flow route is through an analyzer region of another FAIMS device, which other FAIMS device is disposed intermediate the ionization source and the ion inlet. Accordingly, communicating is not intended to include remote communication with an ionization source, in which there is a statistically low probability of ions propagating from the ionization source, through the ion inlet, and into the analyzer region. The reader will appreciate the instant invention, when viewed in the context of prior art.

Figure 1A:
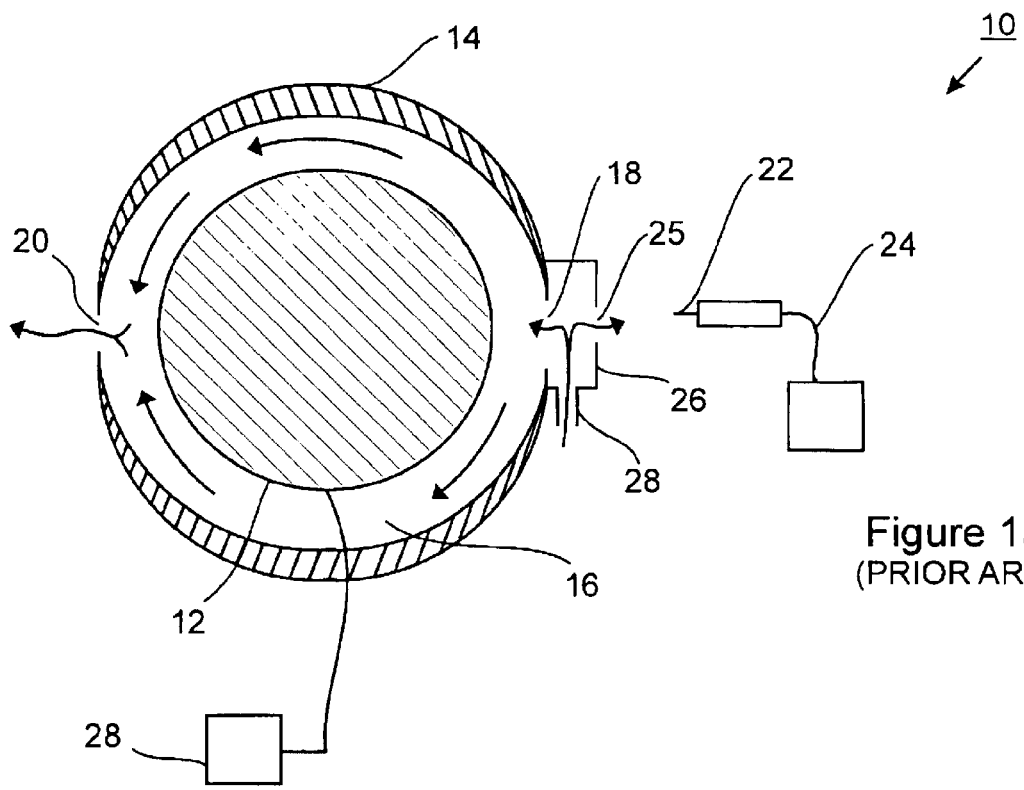
FIG. 1a is a simplified cross sectional end view of a cylindrical side-to-side FAIMS device according to the prior art.

Referring to FIG. 1a, shown is a simplified cross sectional end view of a cylindrical side-to-side FAIMS according to the prior art. The cylindrical side-to-side FAIMS device, shown generally at 10, includes inner and outer cylindrical electrodes 12 and 14, respectively, which are supported by an electrically insulating material (not shown) in an overlapping, spaced-apart arrangement. The generally annular space between the inner electrode 12 and the outer electrode 14 defines a FAIMS analyzer region 16. The analyzer region 16 is of approximately uniform width and extends around the circumference of the inner electrode 12. An ion inlet 18 is provided through the outer electrode 14 for introducing ions from an ion source into the analyzer region 16. For example, the ion source is in the form of an electrospray ionization ion source including a liquid delivery capillary 24, a fine-tipped electrospray needle 22 that is held at high voltage (power supply not shown) and a curtain plate 26 serving as a counter-electrode for the electrospray needle 22. Of course, any other suitable ionization source is optionally used in place of the electrospray ionization ion source. A flow of a carrier gas, which is represented in the figure by a series of closed-headed arrows, is provided within the analyzer region 16 to carry the ions around the inner electrode 12 and toward an ion outlet 20. An orifice 25 within the curtain plate electrode 26 allows for a portion of the carrier gas introduced at gas inlet 28 to flow in a direction that is counter-current to the direction in which the ions are traveling near the ion inlet 18, so as to desolvate the ions before they are introduced into the analyzer region 16. The inner electrode 12 is in electrical communication with a power supply 28 that during use is capable of applying a high voltage asymmetric waveform (DV) and a low voltage dc compensation voltage (CV) to the inner FAIMS electrode 12.

Still referring to FIG. 1a, ions are produced in the gas phase at the fine-tipped electrospray needle 22 from a suitable sample containing a species of interest. Typically, a mixture including a plurality of different ion types is produced when the sample is ionized. The potential gradient pushes the ions of the mixture away from the electrospray needle 22, toward the curtain plate electrode 26. A portion of the ions pass through the orifice 25 in the curtain plate electrode 26, become entrained in the carrier gas flow and are carried into the FAIMS analyzer region 16. Once inside the FAIMS analyzer region 16, the ions are carried through an electric field that is formed within the FAIMS analyzer region 16 by the application of the DV and the CV to the inner FAIMS electrode 12. Ion separation occurs within the FAIMS analyzer region 16 on the basis of the high field mobility properties of the ions. Those ions of the mixture that have a stable trajectory for a particular combination of DV and CV are selectively transmitted through the FAIMS analyzer region 16, whilst other ions of the mixture collide with an electrode surface and are lost. The selectively transmitted ions are extracted from the analyzer region 16 via ion outlet 20 and are typically subjected to one of detection and further analysis.

Figure 1B:
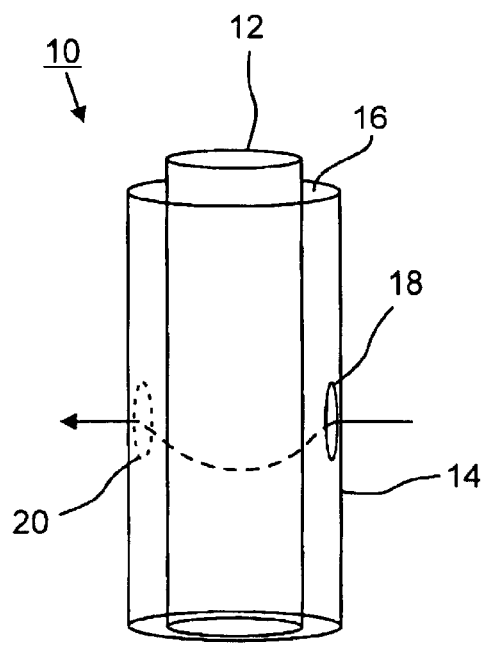

Referring now to FIG. 1b, shown is a simplified side elevational view of the cylindrical side-to-side FAIMS of FIG. 1a. Elements labeled with the same numerals have the same function as those illustrated in FIG. 1a. The dotted line extending between ion inlet 18 and ion outlet 20 represents one possible average ion flow path around the inner electrode 12. An average ion flow path is defined as the net trajectory of an ion as a result of a carrier gas flow through the analyzer region, although the individual ion also experiences an oscillatory motion between the electrodes as a result of the applied asymmetric waveform voltage. In particular, the dotted line represents one of two shortest average ion flow paths through the analyzer region 16, one shortest average ion flow path extending in each direction around the inner electrode 12. Of course, when many like-charged ions are present within the analyzer region, ion-ion repulsion forces tend to cause the ions to spread out slightly along the length of the inner electrode 12. Accordingly, some selectively transmitted ions migrate into portions of the analyzer region where the gas flow rate is low or stagnant, making their extraction from the analyzer region difficult.

Figure 2A:
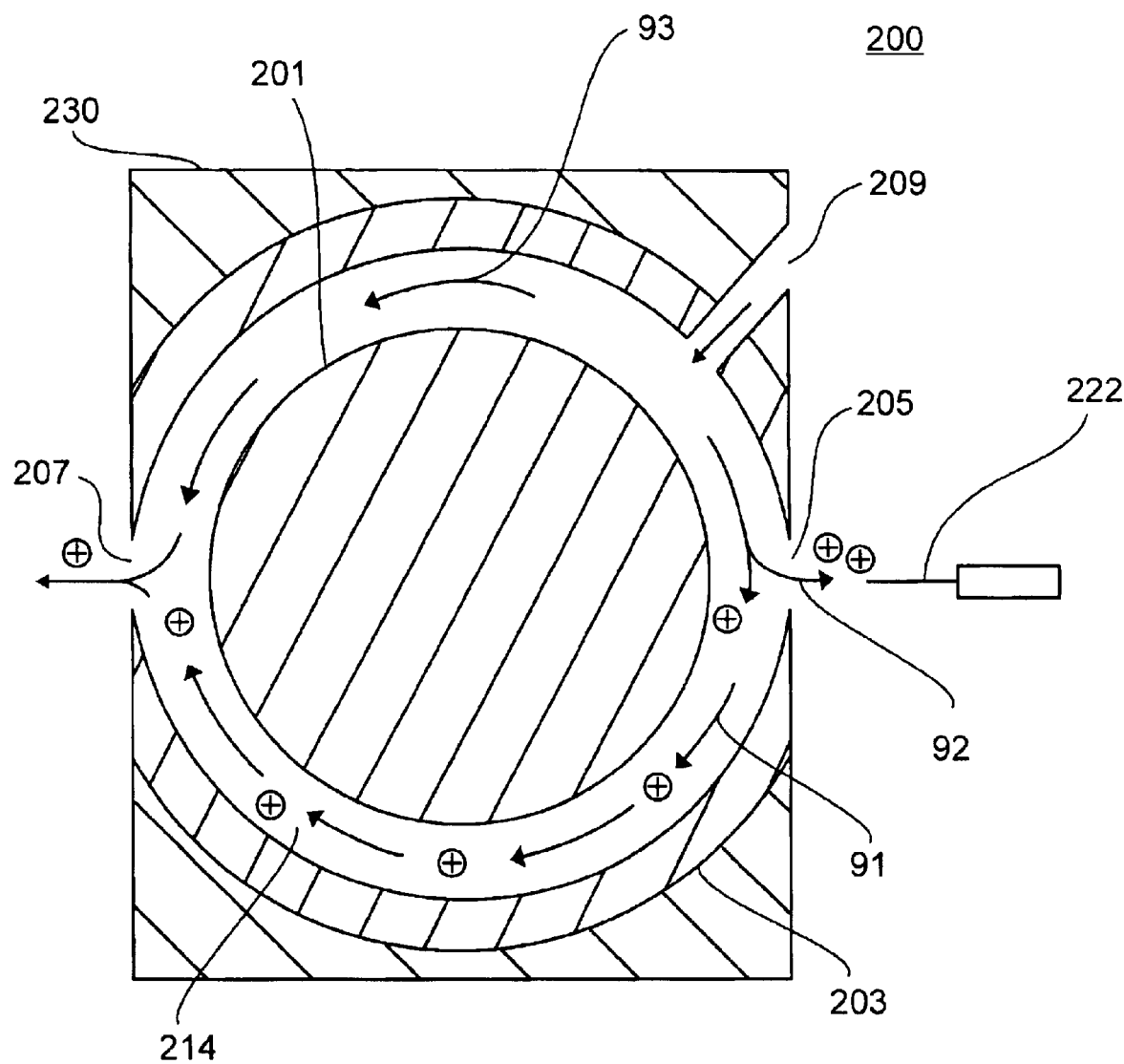
FIG. 2a shows a simplified cross sectional end view of a FAIMS device without a separate desolvation chamber and having a gas inlet positioned in close proximity to an ion inlet.

Referring now to FIG. 2a, shown is a simplified cross sectional end view of FAIMS device without a separate desolvation chamber and having a gas inlet positioned in close proximity to an ion inlet. A FAIMS device 200 includes an inner electrode 201, and outer electrode 203, an ion inlet 205 as well as an ion outlet 207. The inner and outer electrodes are for example provided as solid cylinder and cylindrical pipe, respectively. In general, the inner electrode has a length and an outer circumference, whereas the outer electrode has a length and an inner circumference. The inlet and outlet are for example provided in the form of one of an orifice and a slit. The components of the FAIMS device are embedded in an insulating material 230 such as polyetheretherketone (PEEK), which is used for maintaining the relative position of the electrodes one to the other. Typically, the FAIMS device 200 is in fluid communication with another device, for instance one of a pump and a not illustrated mass spectrometer detector, so that a gas flow is pulled through the FAIMS device 200 and out of the outlet 207.

Referring still to FIG. 2a, the FAIMS device 200 comprises a second inlet, that is a port for a gas inlet 209 through the wall of outer electrode 203 in the vicinity of the ion inlet 205. Arrows illustrate the gas flows in this first embodiment of the instant invention, the lengths of which are indicative of the difference in the velocity of gas flow rates around the inner electrode 201. A fine-tipped electrospray needle 222 that is held at high voltage (power supply not shown), is one component of the ionization source shown at FIG. 2a. Of course, any other suitable ionization source is used optionally in place of the electrospray ionization source. The gas introduced via the gas inlet 209 into the FAIMS device splits into two flows. One of the flows, the extra gas flow 93 travels around one side of the inner electrode toward the ion outlet 207. The other gas flow, comprising both the desolvation gas flow 92 and the carrier gas flow 91, travels in a direction around the other side of the inner electrode toward the ion inlet 205. In a region near the ion inlet 205 the other gas flow further splits into two flows, the desolvation gas flow 92 and the carrier gas flow 91. The desolvation gas flow 92 functions to desolvate the electrosprayed ions as they travel through the ion inlet 205 toward the analyzer region 214. This desolvation process reduces the amount of solvent and other contaminants that enter the FAIMS analyzer region and eliminates the need for a curtain plate assembly.

Ions are able to pass through the counter-current flow of desolvation gas 92 and into the FAIMS analyzer region 214 because of the electric field produced by the high voltage that is applied to the ionization source. The high voltage applied to the electrospray needle 222, in addition to producing an intensely strong electric field that creates conditions necessary to ionize the components of a liquid sample, also results in a strong electric field that directs electrosprayed ions of the appropriate charge polarity away from the electrospray needle 222 and toward the outer electrode 203 that serves as the counter electrode for the electrospray needle 222. Some of the ions pass through the ion inlet 205 of the FAIMS device. The carrier gas flow 91 transports ions around the inner electrode 201 and toward the ion outlet 207. Those ions which are selectively transmitted through the analyzer region 214, for the particular combination of DV and CV that is applied to the FAIMS electrodes, are extracted from the analyzer region 214 via the ion outlet 207.

In the FAIMS device 200 shown at FIG. 2a, ions passing through the ion inlet 205 and entering the analyzer region 214 travel around only one side of the inner electrode 201. The gas flow entering the FAIMS device through the gas inlet 209 and flowing in a direction toward the ion inlet 205 substantially prevents a flow of ions from traveling in a direction from the ion inlet 205 toward the gas inlet 209. In addition, the total volume of gas flow through the ion outlet 207 is equal to the sum of carrier gas flow 91 and extra gas flow 93. The distance between the gas inlet 209, and the ion outlet 207 is shorter in one direction (counter clockwise in the example of FIG. 2a) than in the other (clockwise in the example of FIG. 2a). That is the distance that the extra gas flow 93 travels from the gas inlet 209 to the ion outlet 207 is shorter than the distance that the carrier gas flow 91 travels from the gas inlet 209 to the ion outlet 207. Thus, a velocity of the extra gas flow 93 is higher than a velocity of the carrier gas flow 91. A low carrier gas flow rate translates into a longer transmission time of ions through the analyzer region 214. This in turn leads to an increase in ion loss due to processes such as diffusion and space charge repulsion, both of which are time dependent and therefore, possibly lower ion transmission through the FAIMS device 200.

Figure 2B:
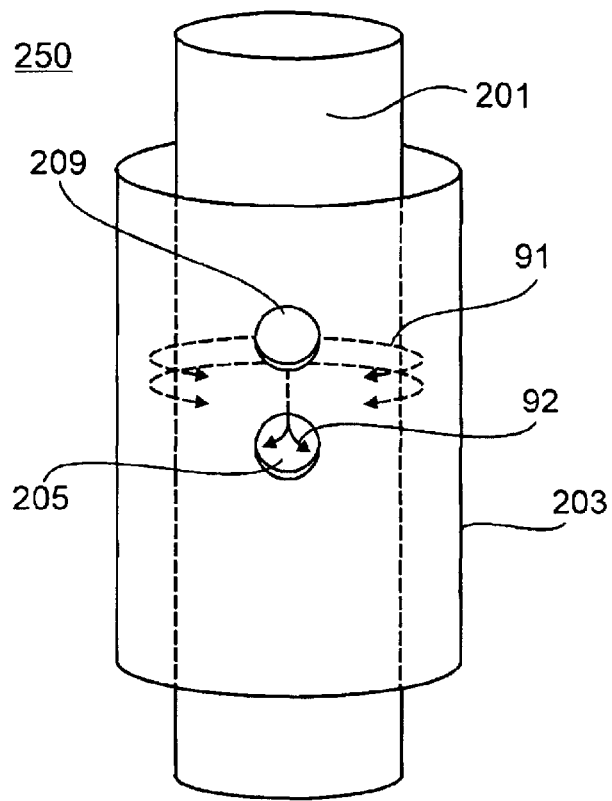
FIG. 2b shows a side elevational view of a side-to-side FAIMS device without separate desolvation region having a gas inlet and an ion inlet both positioned opposite to an ion outlet.
Figure 2C:
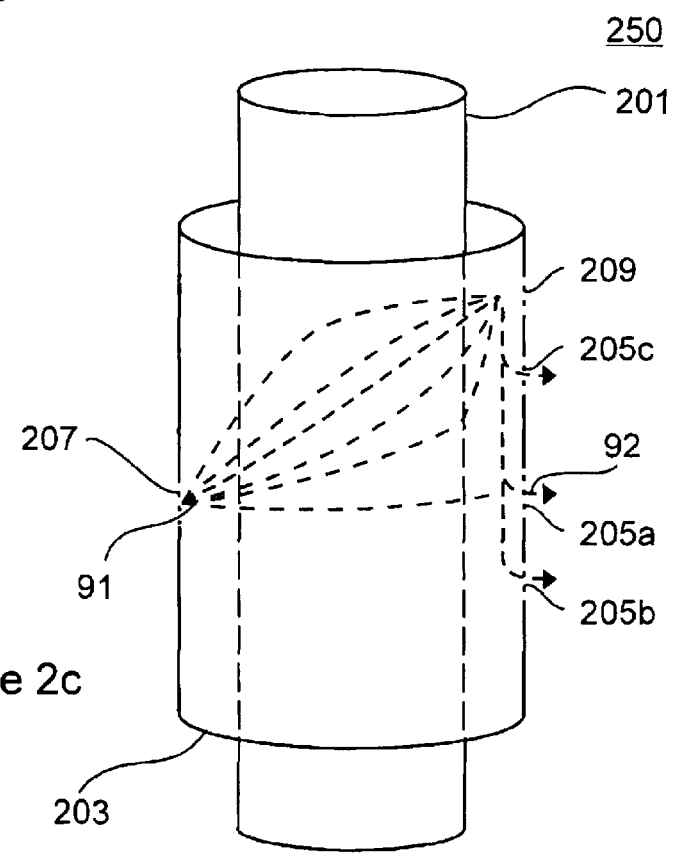
FIG. 2c shows a side elevational view of a side-to-side FAIMS device indicating different positions of an ion inlet relative to a gas inlet and an ion outlet.

Referring now to FIG. 2b, shown is a side elevational view of a side-to-side FAIMS device without separate desolvation region and having a gas inlet and an ion inlet both positioned opposite to an ion outlet. In the FAIMS device shown generally at 250, the gas inlet 209 and the ion inlet 205 are positioned at 180° from the ion outlet (not shown). The ion inlet 205 and the gas inlet 209 are adjacent to each other, but rather than being adjacent along a circumference of a cylindrical outer electrode 203 as in FIG. 2a, the ion inlet 205 and the gas inlet 209 are adjacent to each other along a longitudinal length of the outer electrode 203. This positioning of the inlets supports a carrier gas flow 91 around both sides of an inner electrode 201, with an approximately same carrier gas flow rate in both directions around the inner electrode 201 in a direction toward the not illustrated ion outlet. In FIG. 2c, shown are three possible locations 205a, 205b, and 205c for an ion inlet 205. Since the gas inlet 209 is not placed at the same location along the length of the outer electrode 205 as the ion outlet 207, gas exiting the FAIMS device 250 at the ion outlet 207 will travel around the inner electrode 201 as is shown schematically in FIG. 2c. The preferred gas flow path depends on variables such as gas flow rates exiting the analyzer region via the ion inlet and the ion outlet. When the ion inlet 205 is not positioned between the ion outlet 207 and the gas inlet 209 with reference to the main axis, for example at ion inlet position 205b, ions that have entered the FAIMS device 250 experience only a counter-flow of gas which prevents the ions from traveling around the inner electrode to the ion outlet. When the ion inlet 205 is placed between the ion outlet 207 and the gas inlet 209 with reference to the main axis, i.e. at ion inlet position 205c, ions that enter the FAIMS device become entrained in the carrier gas flow and are transported by the carrier gas around the inner electrode 201 and through the ion outlet 207. Optionally, the gas inlet 209 and the ion inlet 205 are of different size and or shape.

Of course, the figures that are referred to throughout the detailed description are greatly simplified so as to facilitate an understanding of the instant invention. A reader skilled in the art will appreciate that the gas enters and exits the space between the inner and outer electrodes mostly through the ion and gas inlets and outlets.

Figure 3:
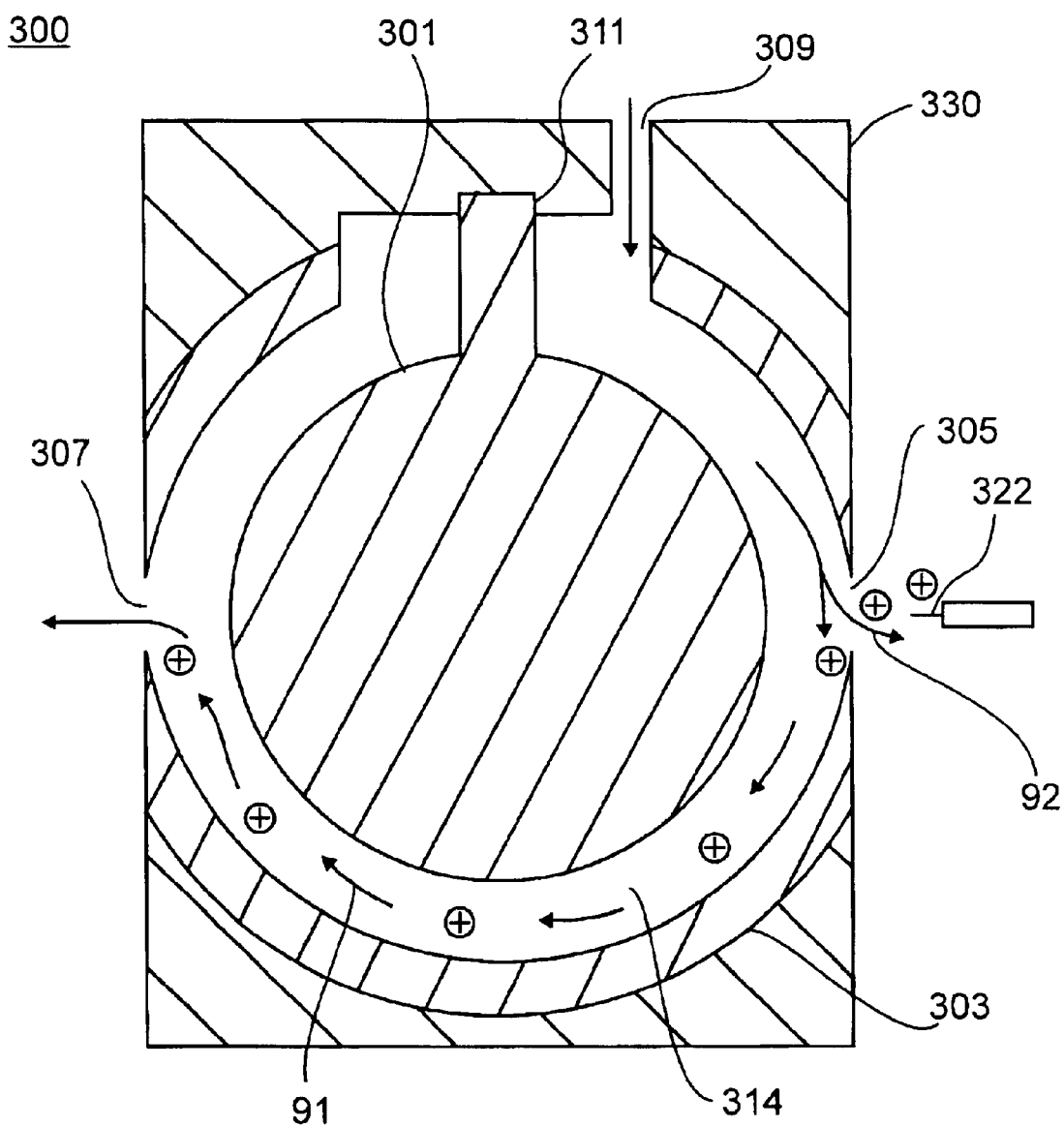
FIG. 3 shows a simplified cross sectional end view of a side-to-side FAIMS device having a protruding gas barrier.

Referring now to FIG. 3, shown is an end view of another FAIMS device without a separate desolvation chamber and having a gas inlet positioned in close proximity to an ion inlet. A FAIMS device 300 includes an inner electrode 301, and outer electrode 303 having an ion inlet 305 and an ion outlet 307. The inner electrode 301 and the outer electrode 303 are supported by an electrically insulating material 330 in an overlapping spaced-apart configuration. Each of the ion inlet and the ion outlet are for example provided in the form of one of an orifice and a slit. Typically, the FAIMS device 300 is coupled to another device, for instance one of a pump and a not illustrated mass spectrometer detector, so that a gas flow is pulled through the FAIMS device 300 and out of the ion outlet 307.

In addition, the FAIMS device 300 comprises a second inlet, that is a port for a gas inlet 309 through the wall of the outer electrode 303 in the vicinity of the ion inlet 305. Further, part of the outer electrode 303 has been cut away to enable a protruding part 311 of the inner electrode 301 to extend into the insulating material 330. Enough of the outer electrode 303 is cut away to leave a wide enough physical space between the electrodes so as to prevent electrical discharge between the inner electrode 301 and the outer electrode 303. The shape of the protruding part 311 is optionally varied. Further optionally, the inner electrode is provided as cylindrical electrode, and the protruding part is provided by a protruding segment of the electrically insulating material 330.

The protruding part 311 of the inner electrode 301 forms an approximately gas tight seal with the electrically insulating material 330 to form a physical barrier which forces the gas flow, which is represented in the figure by a series of closed headed arrows, around one side of the inner electrode 301. Gas entering the FAIMS device 300 through the gas inlet 309 is forced to flow in one direction, the direction toward the ion inlet 305. Unlike the FAIMS device 200 described with reference to FIG. 2a, no extra gas flow is produced in the instant embodiment. Accordingly, the total gas flow exiting at the ion outlet 307 is equal to the carrier gas flow 91. Near the ion inlet 305, the gas flow splits with a portion of the gas going out toward the electrospray needle 322 and constituting the desolvation gas flow 92. The other portion, the carrier gas flow 91, continues through the FAIMS analyzer region 314, around the inner electrode 301, and transports entrained ions to the ion outlet 307.

Optionally the protruding part provides a small gas channel that results in a small controlled extra gas flow traveling towards the ion outlet around the portion of the inner electrode that is not in communication with the ion inlet.

The blockage of flow by the modification of the inner and outer electrodes 301 and 303, respectively, results in changes in the electric fields near the modified region, causing suboptimal conditions for transmission of ions. Therefore, the blockage is advantageously located in a region away from the ion path through the FAIMS device 300 so that the changes in the electric fields caused by the protruding part 311 induce a minimal effect upon the electric fields that ions experience during their transit from the ion inlet 305 to the ion outlet 307.

The presence of the protruding part 311 not only increases carrier gas flow velocities, but also increases an intensity of an ion stream exiting the FAIMS device at the outlet 307. Ion loss due to diffusion of ions into a region of the FAIMS device, which is essentially occupied with extra gas, is approximately minimized. Advantageously, FAIMS device 300, although more elaborate and intricate in its construction than the FAIMS device 200 shown at FIG. 2a, supports analysis of an ion beam having initially a low ion concentration.

Figure 4:
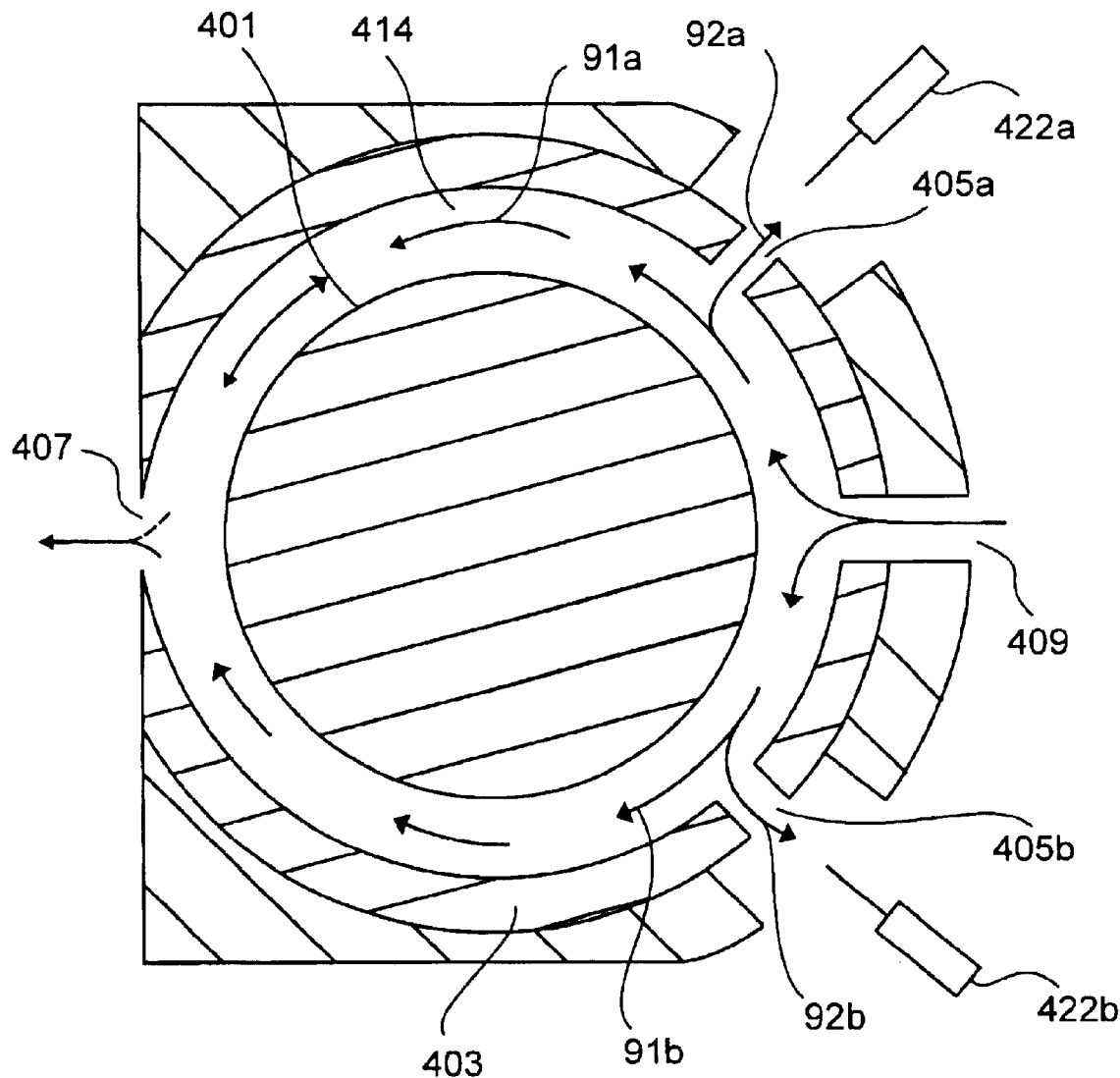
FIG. 4 shows a simplified cross sectional end view of a side-to-side FAIMS device without a separate desolvation chamber and having a gas inlet positioned in close vicinity to two ion inlets.

The concepts for the design of a FAIMS device with a plurality of inlets as outlined above are now applied to FAIMS devices having a plurality of ion inlets. Referring now to FIG. 4, shown is an end view of a first embodiment of the instant invention. A FAIMS device 400 comprises a plurality of ion inlets, each ion inlet of the plurality of ion inlets for being disposed adjacent to a different ion source. More particularly, the FAIMS device 400 includes an inner electrode 401, an outer electrode 403, two ion inlets 405a and 405b, as well as an ion outlet 407. The inner and outer electrodes are for example provided as solid cylinder and cylindrical pipe, respectively. In general, the inner electrode 401 has a length and an outer circumference, whereas the outer electrode 403 has a length and an inner circumference. The inner electrode 401 and the outer electrode 403 are supported by an electrically insulating material 430 in an overlapping spaced-apart configuration. Each of the ion inlet and the ion outlet are for example provided in the form of one of an orifice and a slit. Typically, the FAIMS device 400 is coupled to another device, such as for instance one of a pump and a not illustrated mass spectrometer detector, so that a gas flow is pulled through the FAIMS device 400 and out of the ion outlet 407.

In addition, the FAIMS device 400 comprises a third inlet, namely a port for a gas inlet 409. The gas inlet 409 is positioned such that a flow of gas is introduced at 180° from the ion outlet 407. Gas flows are substantially equal around the two sides of the inner electrode 401. The gas inlet 409, the two ion inlets 405a and 405b, and the ion outlet 407 are all located on the circumference of the outer electrode 403 at one location along the length of the outer electrode 403. The fine-tipped electrospray needles 422a and 422b that are held at high voltage (power supply not shown), each comprise one component of the separate ion sources shown at FIG. 4. The fine-tipped electrospray needles 422a and 422b are positioned in close vicinity to the inlets 405a and 405b, respectively. The ion inlets 405a and 405b are positioned in a way that the gas inlet 409 is located at an approximately intermediate position between the two ion inlets.

Ions produced by an electrospray ionization source are directed toward the corresponding ion inlet by a strong electric field that exists between the electrospray needle tip and the outer electrode. A gas flow entering the gas inlet 409 splits approximately equally into two flows; since the distances to the ion outlet 407 along the two directions around the inner electrode 401 are approximately equal. When the total volume of the gas flow entering the gas inlet 409 exceeds the volume of gas flow out of the ion outlet 407, then a first portion of the excess flow exits outwardly through ion inlet 405a to provide a desolvation gas flow 92a, and a second portion of the excess glow exits outwardly through ion inlet 405b to provide a desolvation gas flow 92b. Provided that the areas of the two ion inlets 405a and 405b are approximately equal, then the volumes of the desolvation gas flow 92a and the desolvation gas flow 92b are approximately equal. The ions that are entering the FAIMS analyzer 414 through ion inlet 405a and 405b therefore pass through a counter-current flow of gas, and are desolvated. Ions that have successfully entered the analyzer region 414 are carried by the carrier gas flows 91a and 91b around the circumference of the inner electrode 401.

The following non-limiting example illustrates a balanced gas flow mode of operation of FAIMS device 400. It is assumed in the instant example that the FAIMS device 400 is coupled to another device causing a flow of gas through the analyzer region 414 and out of the ion outlet 407. If the gas flow out of the outlet 407 is 400 mL/minute, and a flow of approximately 600 mL/minute is pushed into the gas inlet 409, then it is expected that a desolvation gas flow 92a of approximately 100 mL/minute flows out of ion inlet 405a and a desolvation gas flow 92b of approximately 100 mL/minute flows out of ion inlet 405b. In addition, a carrier gas flow 91a of approximately 200 mL/minute flows in the direction from ion inlet 405a towards the ion outlet 407, and a carrier gas flow 91b of approximately equal volume flows between ion inlet 405b and the ion outlet 407. The two flows of 200 mL/minute combine near the ion outlet 407, and a gas flow of 400 mL/minute exits through the ion outlet 407. The flow rates used in this example are illustrative of the operation of the FAIMS device 400. Optimum gas flow rates are possibly determined by experimentation.

The presence of two ion inlets allows for a more efficient use of the FAIMS device 400. When only one ion inlet is used, for example ion inlet 405b, and the other ion inlet 405a is blocked, probe preparation for feeding the electrospray needle 422a can take place, while electrospray needle 422b is producing ions. Once an experiment involving electrospray needle 422b is finished, the functionality of the ion inlets is switched, that is ion inlet 405b is blocked and ion inlet 405a is opened, such that the ions produced at electrospray needle 422a are analyzed. In this way, a continuous utilization of the FAIMS device is achieved, independent of delays relating to probe preparation, sample changes, and the like.

Figure 5A:
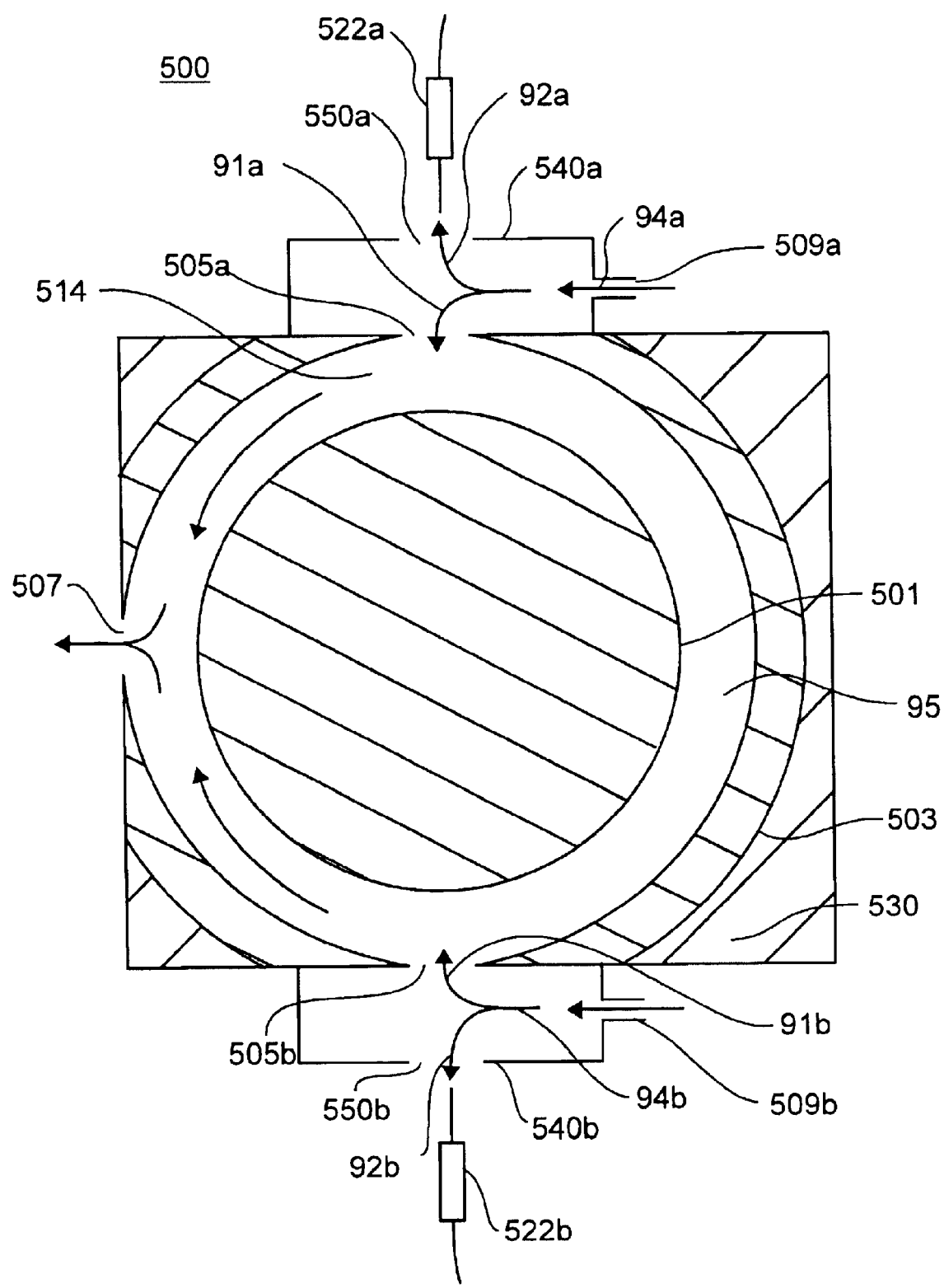
FIG. 5a shows a simplified cross sectional end view of a side-to-side FAIMS device having two ion inlets and two ion sources.

Referring now to FIG. 5a shown is an end view of a second embodiment of the instant invention. FAIMS device 500 comprises a plurality of ion inlets, each ion inlet of the plurality of ion inlets for being disposed adjacent to a different ion source. Some advantages indicated in connection with FAIMS device 400, such as the effective use of multiple ion inlets, are also fully realized in FAIMS device 500. More particularly, the FAIMS device 500 includes an inner electrode 501, an outer electrode 503, two ion inlets 505a and 505b, as well as an ion outlet 507. Preferably, the two ion inlets are positioned approximately at an angle of 180° relative to each other. The ion outlet 507 is preferably positioned in an intermediate position, between the two ion inlets 505a and 505b. The inner and outer electrodes are for example provided as solid cylinder and cylindrical pipe, respectively. In general, the inner electrode 501 has a length and an outer circumference, whereas the outer electrode 503 has a length and an inner circumference. The inner electrode 501 and the outer electrode 503 are supported by an electrically insulating material 530 in an overlapping spaced-apart configuration. Each of the ion inlet and the ion outlet are for example provided in the form of one of an orifice and a slit. Typically, the FAIMS device 500 is coupled to another device, such as for instance one of a pump and a not illustrated mass spectrometer detector, so that a gas flow is pulled through the FAIMS device 500 and out of the outlet 507.

In front of ion inlets 505a and 505b are positioned curtain plate assemblies including curtain plates 540a and 540b, respectively. The curtain plate assemblies include gas inlets 509a and 509b for the introduction of curtain gas flows 94a and 94b, respectively, and for the introduction of ion streams produced by fine-tipped electrospray needles 522a and 522b through curtain plate orifices 550a and 550b, respectively. The curtain plates 540a and 540b serve as counter-electrodes for the fine-tipped electrospray needles 522a and 522b, respectively. Curtain gas flows 94a and 94b introduced into the curtain plate assemblies split into carrier gas flows 91a and 91b flowing through ion inlets 505a and 505b into an analyzer region 514 of FAIMS device 500, and into desolvation gas flows 92a and 92b flowing towards electrospray needles 522a and 522b, respectively, and desolvating ions produced by said electrospray needles. The region between the two ion inlets 505a and 505b that is substantially opposite to the ion outlet 507 comprises a region of stagnant gas 95. In a balanced gas flow mode of operation, very little gas flow takes place in the area occupied by stagnant gas.

If the flow rates of each one of the curtain gas flows 94a and 94b are approximately equal, and assuming that the two ion inlets are of approximately equal area, then gas flows through each ion inlet will also be approximately equal. These operating conditions are appropriate for simultaneous analysis of ions that are produced separately at the two ionization sources. If the rate of curtain gas flow 94a is higher than the rate of curtain gas flow 94b, then the carrier gas flow 91a entering through the ion inlet 505a into the analyzer region 514 will split into a gas flow exiting through the ion outlet 507 and into a gas flow being swept around the analyzer region and exiting through ion inlet 505b, thereby reducing a volume of the carrier gas flow 91b that enters the analyzer region. Consequently, when the rate of curtain gas flow 94a is significantly higher than the rate of curtain gas flow 94b, the FAIMS device 500 acts to analyze ions produced by electrospray needle 522a. On the other hand, when the rate of curtain gas flow 94a is less than the rate of curtain gas flow 94b, the FAIMS device 500 acts to analyze ions produced by electrospray needle 522b. Thus, an appropriate adjustment of the flow rates of the curtain gas flows supports a selective switching between different ion sources, or different combinations of ion sources, of a plurality of ion sources. Of course, the ions from both electrospray sources must have appropriate ion mobility properties for being transmitted through the analyzer region 514 with a same applied CV and DV. Optionally, the applied CV and DV are rapidly switched during a period of time approximately coinciding with the switching between one source and the other, so as to provide appropriate conditions for selectively transmitting an ion of interest produced at the selected source. Further optionally, one of the ionization sources is other than an electrospray source, such as for instance corona discharge, radioactive foil, photoionization source, laser source, and the like.

Figure 5B:
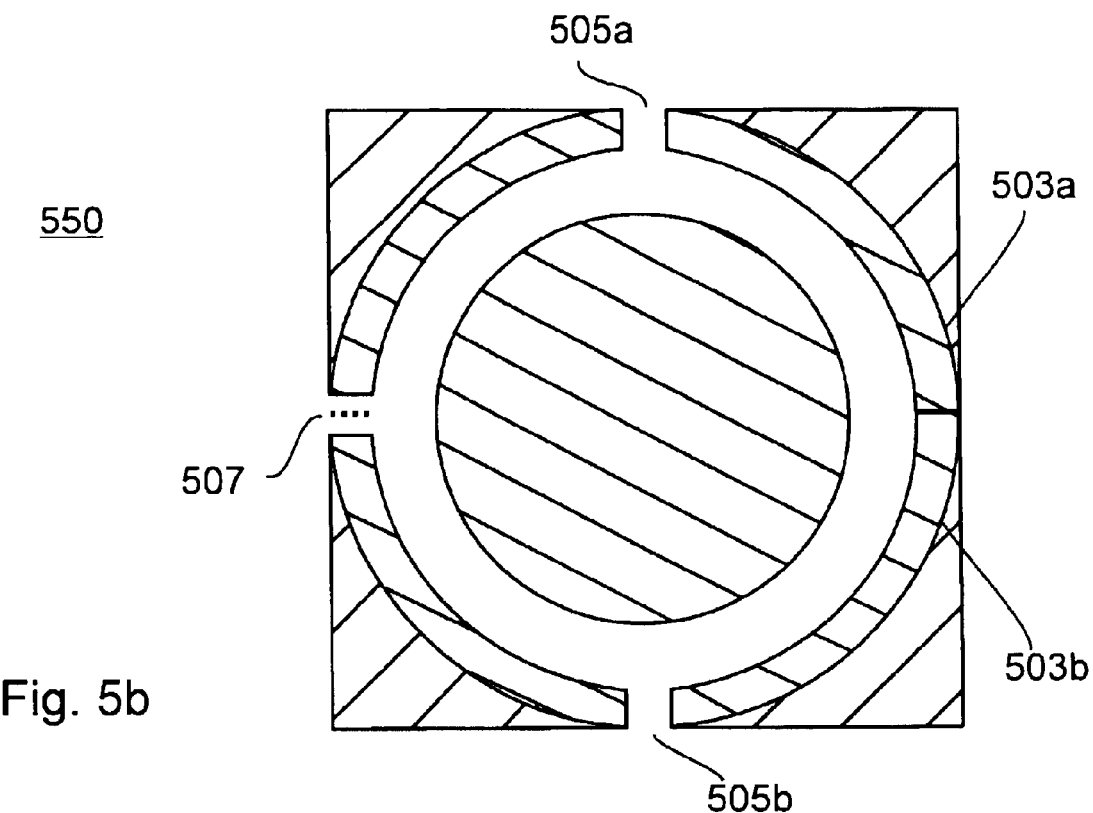
FIG. 5b shows a simplified cross sectional end view of side-to-side FAIMS device having a segmented outer electrode.

Referring to FIG. 5b, shown is a FAIMS device 550, in which the outer electrode is divided into two separate electrically isolated semi-electrodes 503a and 503b. Accordingly, different operating conditions may be imposed, for example by applying different voltages to the different semi-electrodes 503a and 503b, upon the ions traveling from the ion inlets 505a and 505b, respectively, to the ion outlet 507.

Figure 5C:
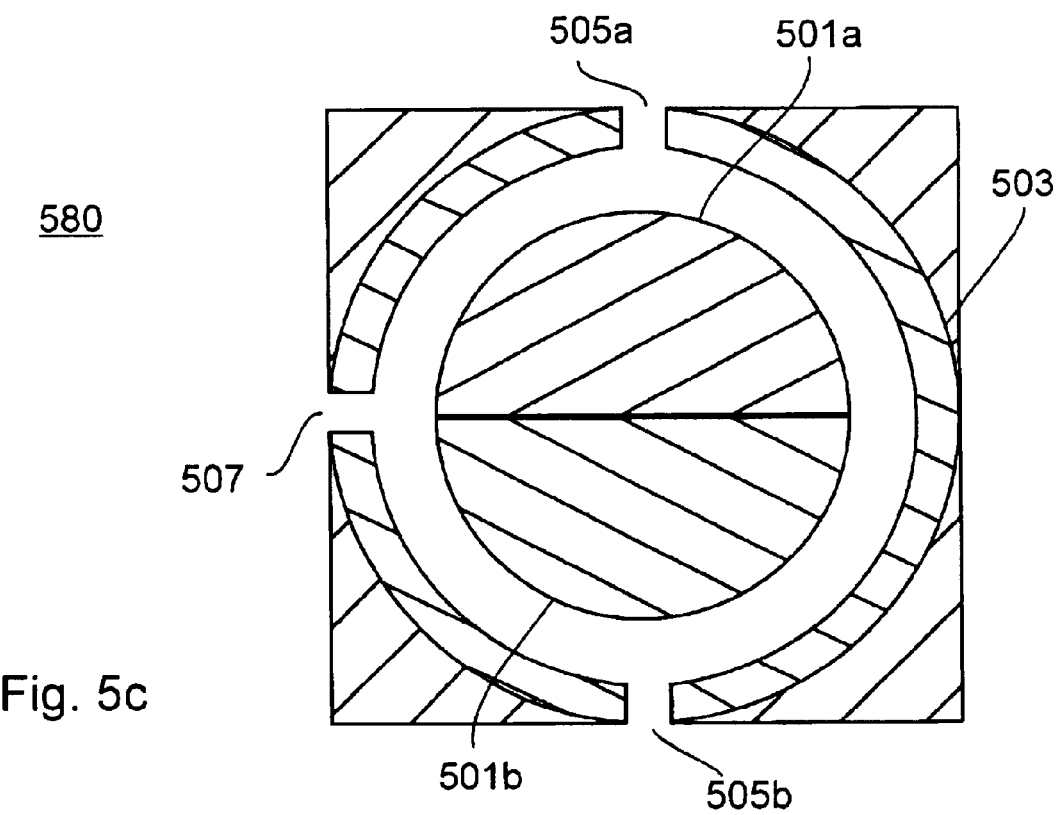
FIG. 5c shows a simplified cross sectional end view of side-to-side FAIMS device having a segmented inner electrode.

Referring now to FIG. 5c, shown is a FAIMS device 580, in which the inner electrode is divided into two separate electrically isolated semi-electrodes 501a and 501b. As was described with reference to FIG. 5b, different operating conditions may be imposed, for example by applying different voltages to the different semi-electrodes 501a and 501b, upon the ions traveling from the ion inlets 505a and 505b, respectively, to the ion outlet 507 Similar considerations apply to FAIMS device 400, shown at FIG. 4.

Figure 6A:
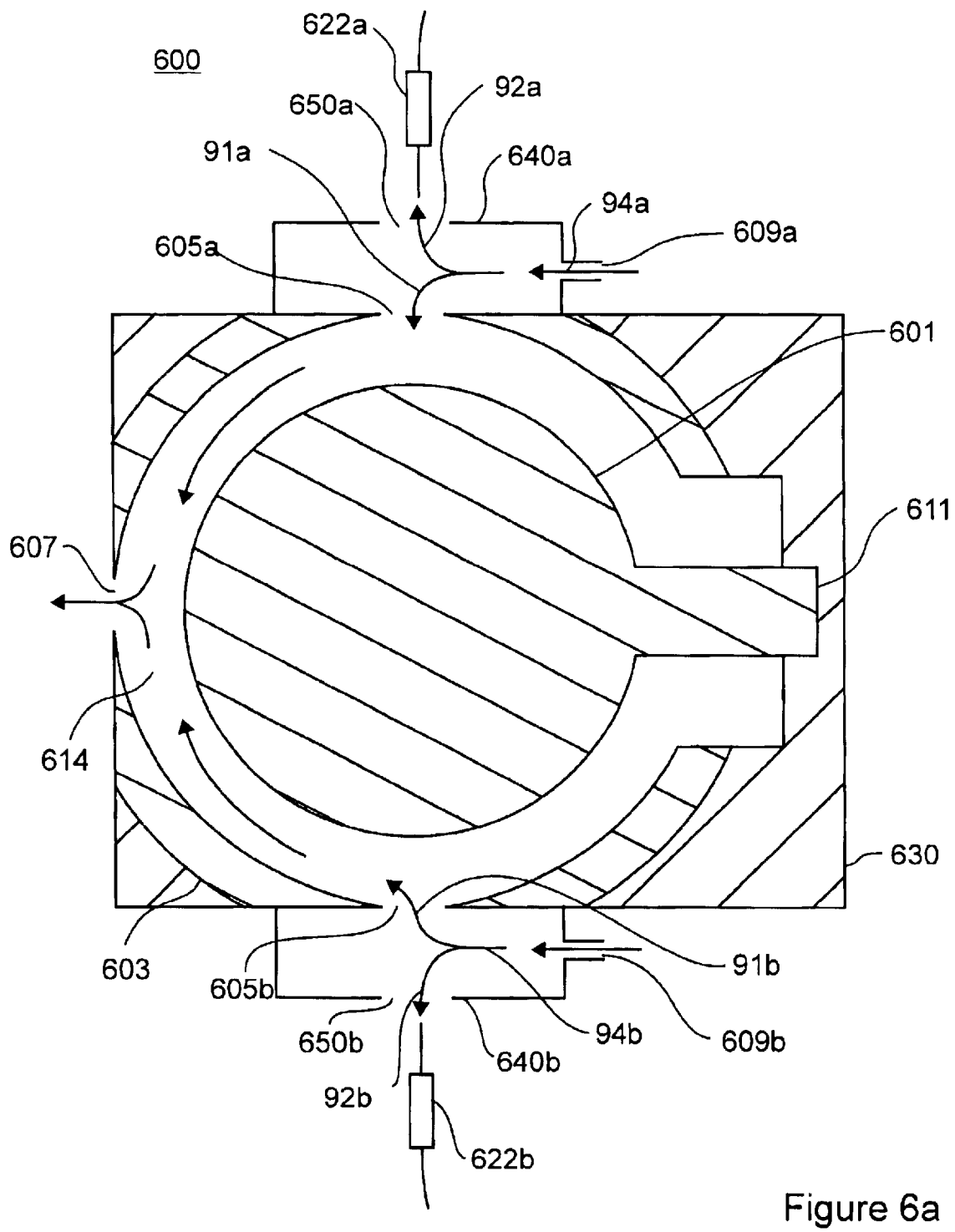
FIG. 6a shows a simplified cross sectional end view of a side-to-side FAIMS device having two ion inlets and two ion sources, and having a protruding gas barrier.

Referring now to FIG. 6a shown is an end view of another FAIMS device according to the instant invention. FAIMS device 600 comprises multiple inlets for ions and/or gases. More particularly, the FAIMS device 600 includes an inner electrode 601, an outer electrode 603, two ion inlets 605a and 605b, as well as an ion outlet 607. Preferably, the two ion inlets are positioned approximately at an angle of 180° relative to each other. The ion outlet 607 is preferably positioned in an intermediate position between the two ion inlets 605a and 605b. The inner and outer electrodes are for example provided as solid cylinder and cylindrical pipe. In general, the inner electrode 601 has a length and an outer circumference, whereas the outer electrode 603 has a length and an inner circumference. The inner electrode 601 and the outer electrode 603 are supported by an electrically insulating material 630 in an overlapping spaced-apart configuration. Each of the ion inlet and the ion outlet are for example provided in the form of one of an orifice and a slit. Typically, the FAIMS device 600 is coupled to another device, such as for instance one of a pump and a not illustrated mass spectrometer detector, so that a gas flow is pulled through the FAIMS device 600 and out of the outlet 607.

In front of ion inlets 605a and 605b are positioned curtain plate assemblies including curtain plates 640a and 640b, respectively. The curtain plate assemblies include gas inlets 609a and 609b for the introduction of curtain gas flows 94a and 94b, respectively, and for the introduction of ion streams produced by fine-tipped electrospray needles 622a and 622b through curtain plate orifices 650a and 650b, respectively. The curtain plates 640a and 640b serve as counter-electrodes for the fine-tipped electrospray needles 622a and 622b, respectively. Curtain gas flows 94a and 94b introduced into the curtain plate assemblies split into carrier gas flows 91a and 91b flowing through ion inlets 605a and 605b into an analyzer region 614 of FAIMS device 600, and into desolvation gas flows 92a and 92b flowing towards electrospray needles 622a and 622b, respectively, and desolvating ions produced by said electrospray needles.

Further, part of the outer electrode 603 has been cut away to enable a protruding part 611 of the inner electrode 601 to extend into the insulating material 630 at a position opposite the ion outlet 607. Enough of the outer electrode is cut away to leave a wide enough physical space between the electrodes so as to prevent electrical discharge between the inner and outer electrodes. Optionally, the inner electrode is provided as a cylindrical electrode, and the protruding part is provided as a protruding segment of the electrically insulating material.

Figure 6B:
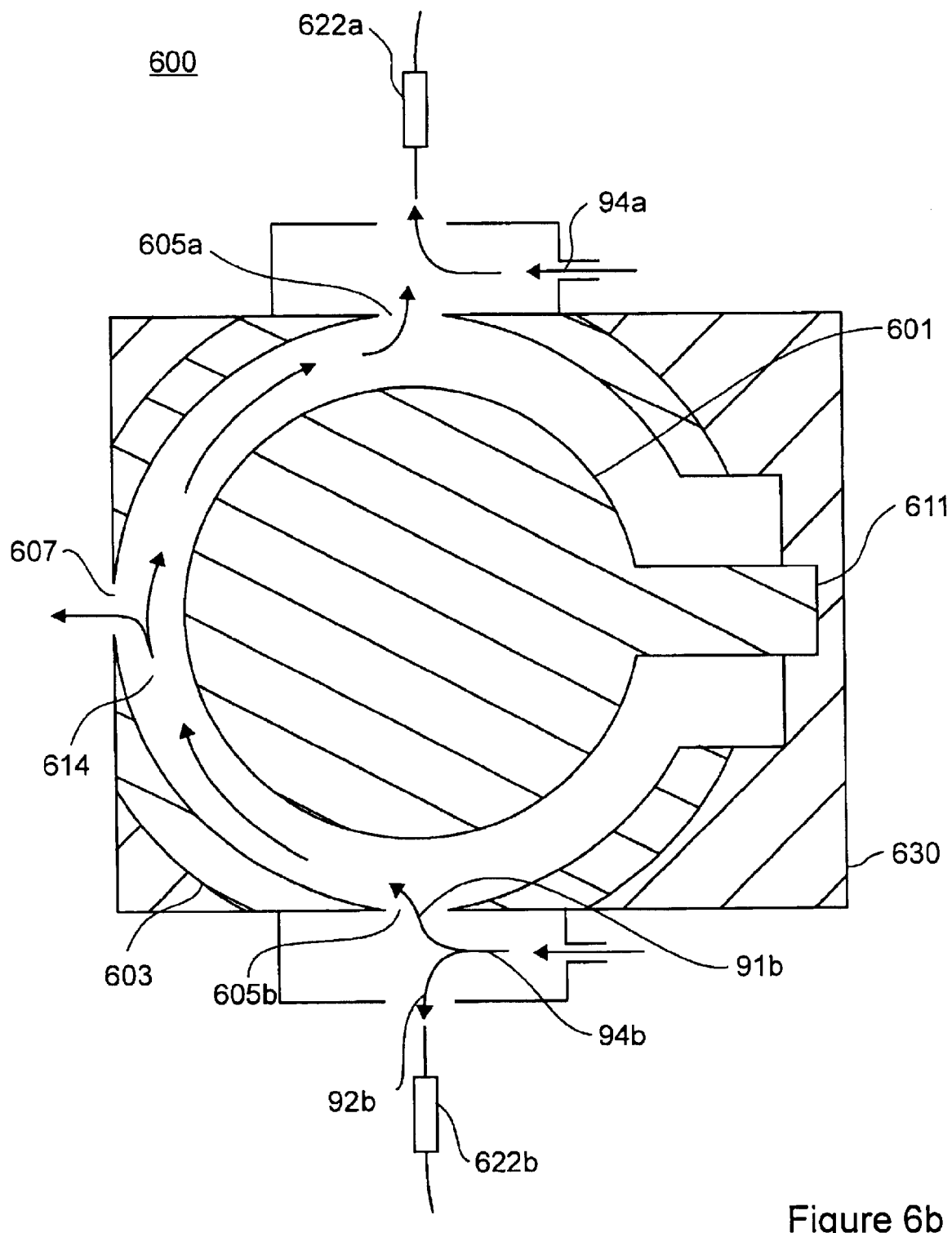
FIG. 6b shows the FAIMS device of FIG. 6a when operating in a different mode.

Referring now to FIG. 6b, it is shown that the FAIMS device 600 also supports a selective switching between different ion sources, in a manner similar to that of the FAIMS device 500. In the mode of operation that is illustrated at FIG. 6b, curtain gas flow 94b significantly exceeds curtain gas flow 94a. As a result, the direction of gas flow through the ion inlet 605a is reversed compared to that of the balanced flow mode of operation, which is illustrated at FIG. 6a. Hence, ions produced at electrospray needle 622b are carried into the analyzer region 614, whereas ions produced at electrospray needle 622a that are able to enter the analyzer region 614 immediately encounter a gas flow in a direction from the ion outlet 607 toward the ion inlet 605a, which prevents the ions from being transmitted through the analyzer region 614 toward the ion outlet 607.

Of course, the ions from both electrospray sources, which have appropriate ion mobility properties, are transmitted through the analyzer region 614 with a same applied CV and DV. Optionally, the applied CV and DV are rapidly switched during a period of time approximately coinciding with the switching between one source and the other, so as to provide appropriate conditions for selectively transmitting an ion of interest produced at the selected source. Further optionally, one of the ionization sources is other than an electrospray source, such as for instance corona discharge, radioactive foil, photoionization source, laser source, and the like.

Optionally, at least one of the inner and outer electrodes is provided as two electrically isolated halves, such that different operating conditions may be provided for ions traveling from the ion source 622a to the ion outlet 607, and for ions traveling from the ion source 622b to the ion outlet 607. This optional embodiment supports a use of different gases within each half during a same period of operation, since significant mixing would only likely occur near the outlet.

In general, multiple ion inlets may support a mode of operation in which different gases are provided for transmitting ions through different portions of an analyzer region. In the above-mentioned examples, ions from a first ionization source are transmitted around a portion of a first side of the inner electrode by a first type of gas, whilst ions from a second ionization source are transmitted around a portion of a second side of the inner electrode by a second type of gas. Likely, a different combination of CV and DV is required to transmit ions produced at each ionization source, depending upon the mobility properties of the ions, the composition of the gas provided for transmitting the ions, the temperature of the gas, etc. Accordingly, the CV and DV that is applied between the inner electrode and the outer electrode is switched between at least two combinations, so as to analyze ions produced at the two ionization sources during different, non-overlapping periods of time. Optionally, segmented electrodes are provided so as to support the application of different combinations of CV and DV within different portions of the analyzer region during a same overlapping period of time.

The ideas that have been described supra in conjunction with the disclosed embodiments of the instant invention may also be applied to other type of FAIMS geometries, for example to a domed-FAIMS analyzer. Referring now to FIG. 7a, shown is cross sectional side view of a domed-FAIMS device 700 according to the instant invention. The domed FAIMS device 700 comprises an outer electrode 703, which generally has the shape of a cylindrical pipe open at one end and closed on the other end by means of a curved surface closure, in which there is disposed an ion outlet 707. Further, there are disposed four ion inlets 705a, 705c, 705b and 705d (the latter two not shown in FIG. 7a) in the outer electrode 703. In the preferred embodiment, the four ion inlets 705a, 705c, 705b and 705d are spaced at approximately 90° increments around the circumference of the outer electrode 703. Each ion inlet is separately in communication with one of four electrospray ionization sources 722a, 722b, 722c, and 722d (722b and 722d not shown in FIG. 7a). Furthermore, the domed-FAIMS device 700 includes a cylindrical inner electrode 701 having a curved surface terminus 736 proximate the ion outlet 707 of the outer electrode 703. The curved surface terminus 736 is substantially continuous with the cylindrical shape of the inner electrode and is aligned co-axially with the ion outlet 707. Two separate supporting sleeves 730 and 731, which are fabricated using an electrically insulating material, surround the outer electrode 703; each sleeve being fixed in place relative to the outer electrode. As shown in FIG. 7a, the two supporting sleeves 730 and 731 are mounted so as to leave a longitudinal gap 732 therebetween. The gap 732 is aligned with a region of the outer electrode 703 which includes the ion inlets 705a, 705c, 705b and 705d. Preferably, the gap 732 is of approximately uniform width around the circumference of the outer electrode 703.

An ion source selector comprising a conductive cover cylinder of thin metal, herein referred to as a "rotating ring" 777, covers the gap 732 between the supporting sleeves 730 and 731. The rotating ring 777 has an orifice shown as aperture 779, optionally located, by rotation of the rotating ring, adjacent to an ion inlet. The location of the aperture 779 in the rotating ring 777 is not restricted and therefore is placed for optimal sampling efficiency of ions into an ion inlet. The rotating ring 777 is made in a way that it fits snuggly across the gap 732 between the two supporting sleeves 730 and 731. The fit is not so snug, however, as to prevent a motor (not shown) from being able to rotate the ring 777. A curtain gas inlet 717 is provided through the supporting sleeve 730 for providing fluid communication with the gap 732.

Optionally, at least a portion of the rotating ring 777 engages a groove that is formed within one of the supporting sleeves 730 and 731, so as to prevent movement of the rotating ring 777 along the length of the outer electrode 703.

Figure 7C:
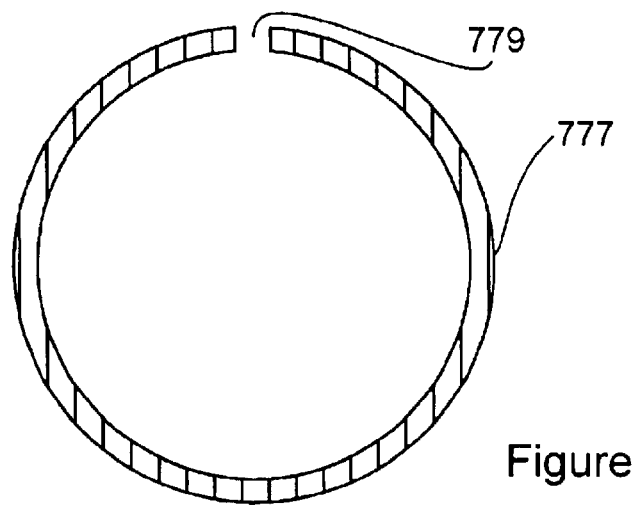
FIG. 7c shows an end view of the rotating ring having an opening.

Optionally, the rotating ring 777 is fabricated from an insulating material with a conductive surface. In FIG. 7b, a side view of the rotating ring 777 is shown, displaying the aperture 779, and in FIG. 7c, an end view of the rotating ring is shown.

Figure 7D:
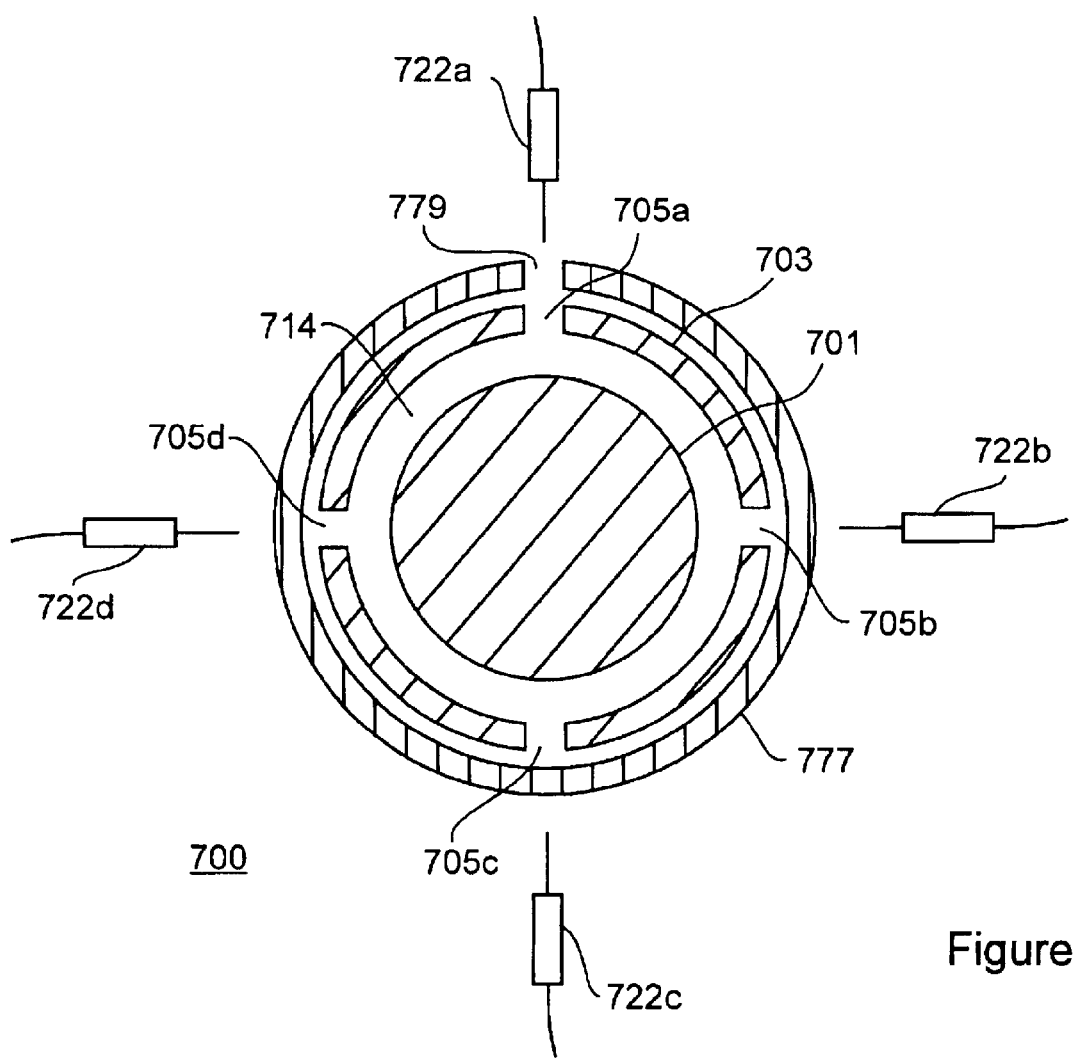

Referring now to FIG. 7d, a cross sectional view of FAIMS device 700 shows the inner electrode 701, the outer electrode 703, the rotating ring 777, the four ion inlets 705a, 705b, 705c, and 705d, as well as the four electrospray ionization sources 722a, 722b, 722c, and 722d. When in operation, all four electrospray ionization sources can spray continuously without interruption since the rotating ring provides a conductive counter electrode necessary for a stable spray. By having only one aperture 779, the rotating ring 777 selectively allows ions from one of the four electrospray ionization sources to pass into the FAIMS device. For example, still referring to FIG. 7d, the aperture 779 is aligned with ion inlet 705a and allows ions produced by electrospray ionization source 722a to enter the analyzer region 714.

Referring to FIGS. 7e, 7f, 7g, and 7h shown is the rotating ring 777 in positions to select ions from each of the various electrospray ionization sources 722a, 722b, 722c, and 722d, respectively. When the aperture 779 in the rotating ring 777 is adjacent to a particular electrospray ionization source, curtain gas that is pumped into the curtain gas inlet 717 as shown in FIG. 7a, exits in part through the aperture 779 in the rotating ring 777 to assist in desolvating ions being produced by the selected electrospray ionization source. Since the other electrospray needles are adjacent to a part of the rotating ring that does not have an aperture therethrough, no desolvation gas is available nor is any desolvation gas needed.

Referring again to FIG. 7a, the curtain gas introduced into curtain gas inlet 717, and thus into the gap 732 between supporting sleeves 730 and 731, is able to flow freely in a circumferential direction within the annular channel that is defined between the gap 732 and the rotating ring 777. This curtain gas flow splits so that a portion of the gas flows toward an electrospray ionization source (not shown) through the aperture 779 and the remaining portion of the gas flows through the four ion inlets 705a, 705b, 705c, and 705d into the analyzer region 714. Gas flowing through ion inlet 705a transports ions from the electrospray ionization source 722a (not shown) into the FAIMS device and toward the ion outlet 707.

Still referring to FIG. 7a, optionally the other three ion inlets 705b, 705c, and 705d through the outer wall of the outer electrode 703 are plugged so as to prevent gas from entering the analyzer region therethrough. For example, the rotating ring 777 comprises plugs that are attached to the inner surface of the rotating ring 777, and located appropriately for covering three ion inlets in the outer electrode 703, when the aperture 779 is positioned adjacent to the fourth ion inlet. In operation, the plugs move together with the rotating ring 777. The plugs are preferably made from an electrically insulating material so as to isolate the conductive surface of the rotating ring 777 from the outer electrode.

Figure 7E:
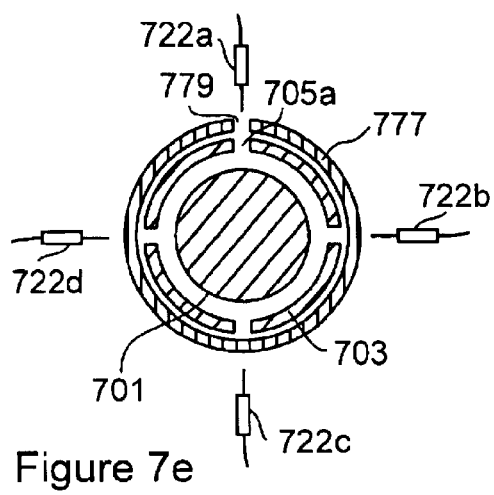
FIG. 7e shows a cross sectional end view of the FAIMS device of FIG. 7a with the opening in the rotating ring in alignment with a first ionization source.
Figure 7F:
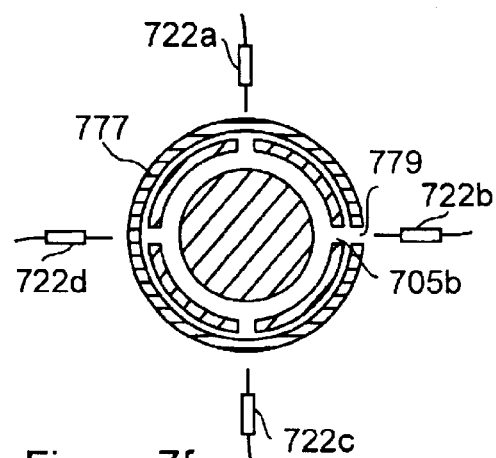
FIG. 7f shows a cross sectional end view of the FAIMS device of FIG. 7a with the opening in the rotating ring in alignment with a second ionization source.
Figure 7G:
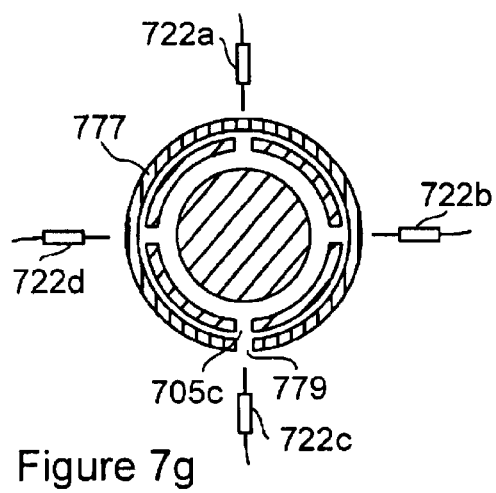
FIG. 7g shows a cross sectional end view of the FAIMS device of FIG. 7a with the opening in the rotating ring in alignment with a third ionization source.
Figure 7H:
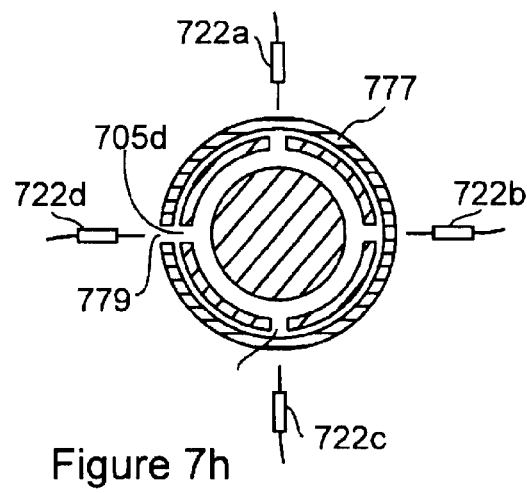
FIG. 7h shows a cross sectional end view of the FAIMS device of FIG. 7a with the opening in the rotating ring in alignment with a fourth ionization source.

To analyze samples from four ionization sources with the FAIMS device 700, the aperture 779 of the rotating ring 777 is rotated in increments of approximately 90° each, stopping for a predetermined period of time in front of each one of the four ionization sources. Referring again to FIGS. 7e, 7f, 7g, and 7h, one specific and non-limiting example is described for analyzing four samples. At time t=0 ms, ions from electrospray ionization source 722a are analyzed (FIG. 7e). After a period of time for analysis, for example 300 ms, the rotating ring 777 is rotated to align aperture 779 with ion inlet 705b, and ions from electrospray ionization source 722b are analyzed (FIG. 7f). There is a delay between the time the ring starts to rotate and the time when ions from electrospray ionization source 722b are extracted through ion outlet 707 (not shown). This delay time consists of the time required for the ring to rotate, the time required for the gas flow to equilibrate, and the time required for the ions to transmit through the FAIMS device. A typical delay time is approximately 200 ms. It follows that in the given example ions from electrospray ionization source 522b are analyzed starting at t=500 ms. After another 300 ms of analysis time and another 200 ms of delay time, ions from electrospray ionization source 522c are analyzed starting at t=1000 ms. Similarly, ions from electrospray ionization source 522d are analyzed starting at t=1500 ms. The process of sampling from each of the ionization sources starts over at t=2000 ms. In this example, data from a given electrospray source is collected each 2000 ms. Although the present example uses four electrospray ionization sources, the process of analyzing ion beams stemming from a plurality of electrospray ionization sources works equally as well for an embodiments including more than, or less than four electrospray ionization sources. Furthermore, different ionization source technologies are optionally used at different ion inlets. Other suitable ionization source technologies include but are not limited to: corona discharge; radioactive foil; photoionization; and, laser ionization. Further still, a flow of a different gas, or mixtures of gases, is optionally provided at each inlet. A person of skill in the art will easily envision additional variations and applications for such a FAIMS device having multiple ion inlets.

Optionally, an outer electrode is provided having a single ion inlet, and at least a portion of the outer electrode including the single ion inlet is rotatable for selectively aligning the single ion inlet with one of a plurality of different ion sources disposed at intervals around the outer electrode. In the instant embodiment, the at least a portion of the outer electrode functions as an ion source selector.

Figure 8A:
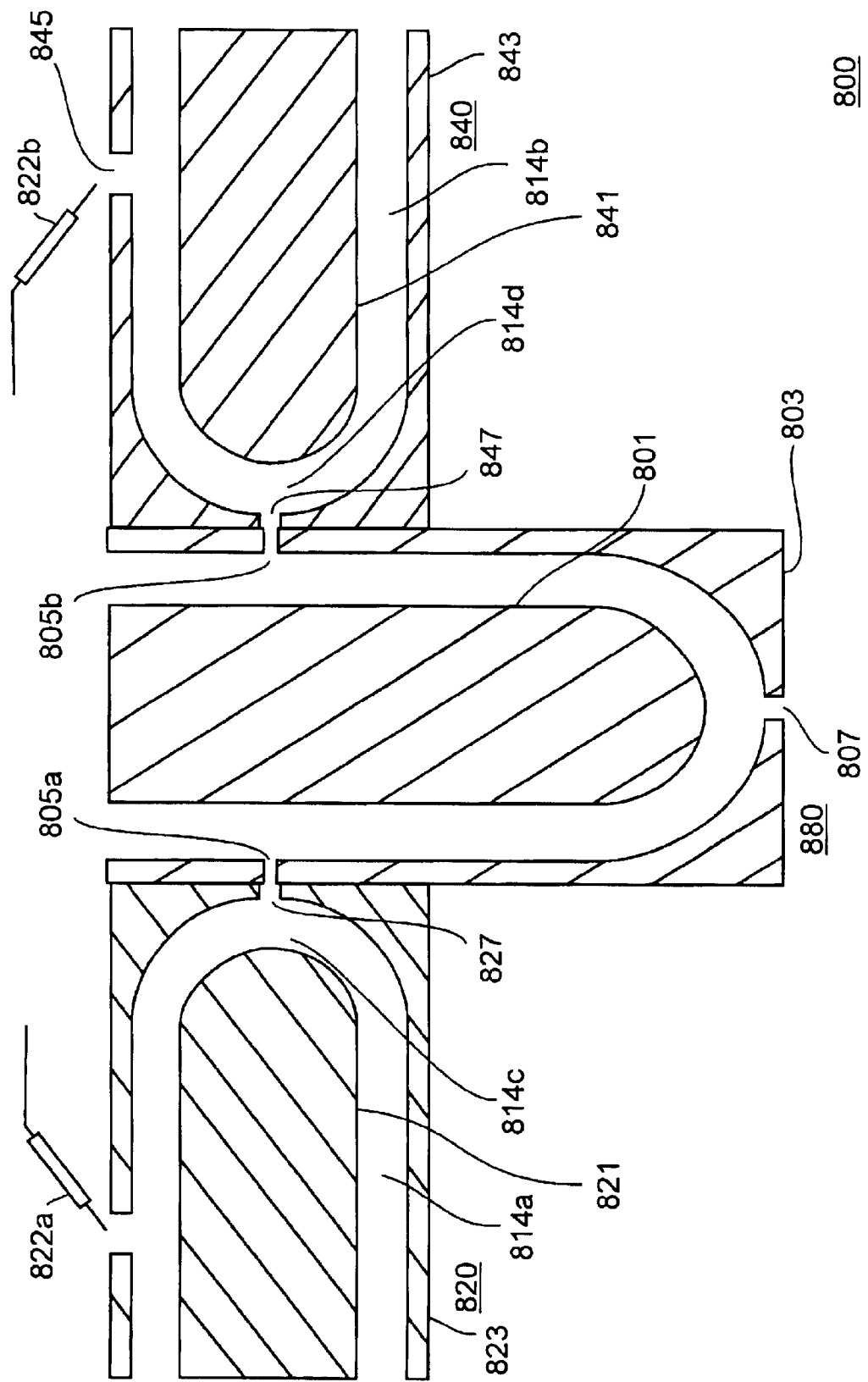
FIG. 8a shows a cross sectional side view of a multiple FAIMS device, including two trapping FAIMS devices that are aligned one each with ion inlets into another FAIMS device.

A FAIMS device including multiple ion inlets optionally supports multiple tandem FAIMS analysis of ions. For example, a first FAIMS device is optionally used as an ion trap, in which ions are stored and subsequently extracted into a second FAIMS device. Conditions for operating a trapping FAIMS device, or tFAIMS, are described. Referring now to FIG. 8a, shown is a cross-sectional view of a multiple FAIMS device according to the instant invention. A multiple FAIMS analyzer 800 comprises two domed tFAIMS 820 and 840, coupled to a third FAIMS 880. The domed tFAIMS 820 and 840 comprise inner electrodes 821 and 841, respectively. Ion outlets 827 and 847 of tFAIMS 820 and 840, respectively, are in communication with ion inlets 805a and 805b of FAIMS 880. An outlet 807 of FAIMS 880 is optionally coupled to a detector or an ion-analyzing device, such as a mass spectrometer. Two ionization sources 822a and 822b provide ions to the tFAIMS 820 and 840, respectively. The functionality of FAIMS 880 is similar to that of other FAIMS devices including multiple ion inlets, herein described previously.

A mode of selectively analyzing ions from the two ionization sources feeding the multiple FAIMS device 800 is described by way of the following non-limiting example. By changing conditions in each trapping tFAIMS device 820 and 840, the respective device is set either to accumulate trapped ions, or to extract trapped ions, the extracted ions being provided into FAIMS device 880. The ionization sources 822*a* and 822*b* are operated continuously so that ions produced by ionization source 822*a* continually enter tFAIMS 820 and ions produced by ionization source 822*b* continually enter tFAIMS 840. Initially, FAIMS operating parameters of gas flows and voltages are selected in tFAIMS 820 and tFAIMS 840 so that the ions of interest from ionization sources 822*a* and 822*b* are accumulated near the hemispherical tips of inner electrodes of tFAIMS 820 and tFAIMS 840, respectively. After a predetermined period of time, referred to as the accumulation time, ions are extracted from a trapping region 814*c* of tFAIMS 820 into FAIMS 880 by changing the conditions from trapping to extraction conditions. For example, the application of a pulsed DC offset voltage to the inner electrode 821 of tFAIMS 820 pushes ions that have been trapped in the vicinity of the tip of hemispherical inner electrode 821 of tFAIMS 820 towards the ion outlet 827. During the extraction of ions from tFAIMS 820, ions from electrospray ionization source 822*b* are still accumulating in the trapping region 814*d* of tFAIMS 840. Ions are extracted from tFAIMS 820 through ion outlet 827 into FAIMS 880 via ion inlet 805*a*, and are transported along the analyzer region of FAIMS 880. Conditions in FAIMS 880 are set so that ions of interest produced at ionization source 822*a* are selectively transmitted. The ions are transported toward the ion outlet 807, which is optionally coupled to one of a detector and an analyzing device. For example, ion outlet 807 is adjacent to an orifice leading to a vacuum chamber of a mass spectrometer (not shown). After ions have been extracted from tFAIMS 820, trapping conditions are restored for tFAIMS 820 and the process of accumulating ions, which are generated by electrospray ionization source 822*a*, in the trapping region of tFAIMS 820 starts again. At a predetermined time, ions from electrospray ionization source 822*b* are extracted from tFAIMS 840 in a similar manner as described above for tFAIMS 820, while ions from electrospray ionization source 822*a* are allowed to accumulate in the trapping region 814*c* of tFAIMS 820. During this extraction process, conditions in FAIMS 880 are such that ions of interest produced at ionization source 822*b* are selectively transmitted.

Still referring to FIG. 8*a*, the conductive outer electrodes 823, 843, and 803 of tFAIMS 820, tFAIMS 840, and FAIMS 880 are shown to be in direct mechanical and electrical contact. Optionally, a narrow insulator separates the three FAIMS devices; however, a gas-tight seal is maintained between the devices to efficiently transmit ions from each of the tFAIMS 820 and 840 into the analyzer region of FAIMS 880. Optionally, transfer between the tFAIMS 820 and 840, and FAIMS 880 is optimized by minimizing a mechanical depth of the ion outlets 827 and 847 to produce a very narrow sharp edged orifice between the devices.

Figure 8B:
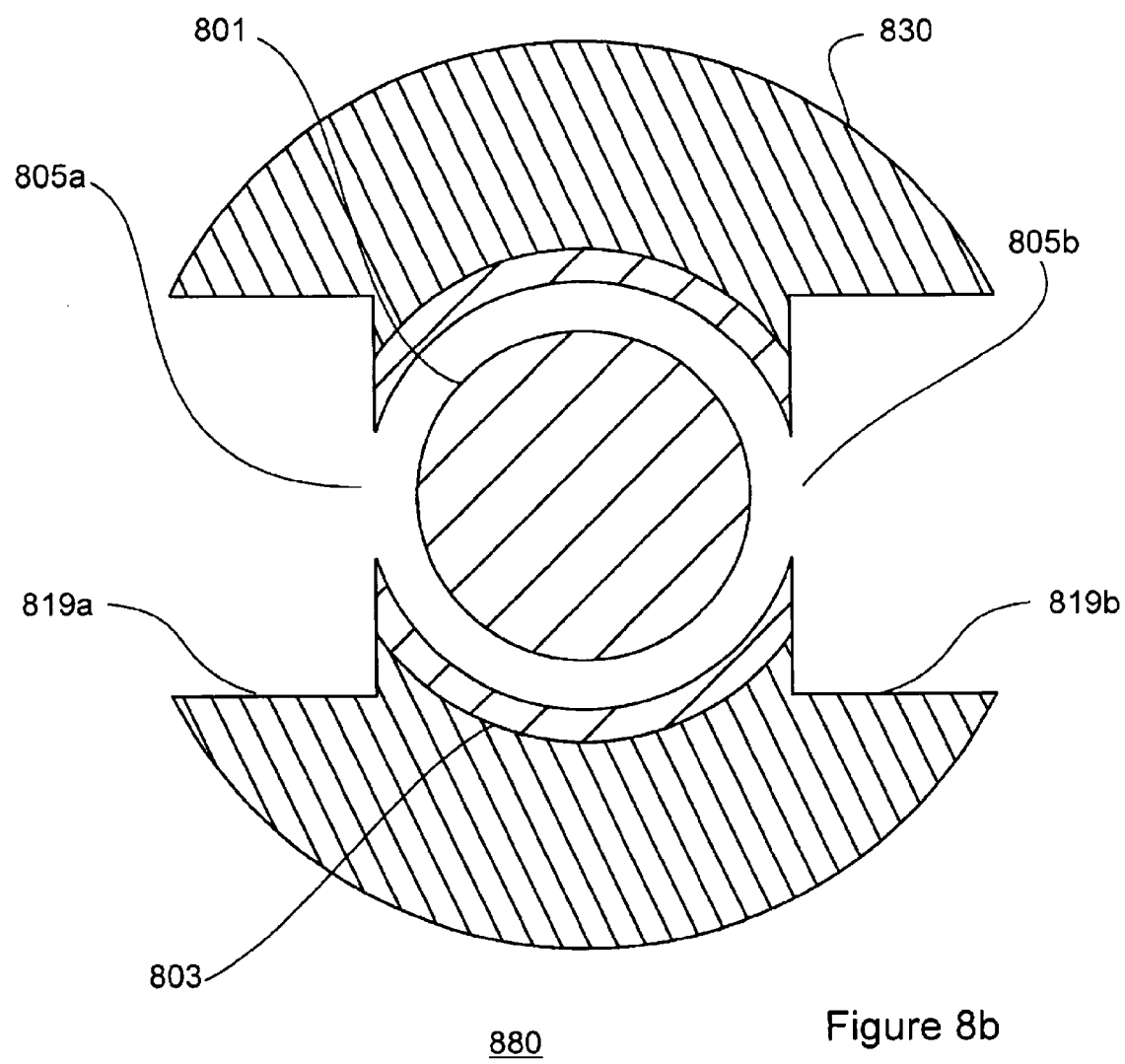
FIG. 8b shows a cross section of the multiple FAIMS device of FIG. 8a taken in isolation at a point where the trapping FAIMS devices align with the ion inlets of the other FAIMS device.

FIG. 8*b* shows a cross section of FAIMS 880 taken in isolation at a point where tFAIMS 820 and 840 align with ion inlets 805*a* and 805*b* of the FAIMS 880. A supporting sleeve 830 made of an electrically insulating material is modified so that the tFAIMS devices 820 and 840 can be fitted into the supporting sleeve. The wall of the outer electrode 803 near the ion inlets 805*a* and 805*b* is very thin. Two cylindrical cavity wells 819*a* and 819*b* are drilled into the supporting sleeve 830. The cylindrical cavity wells 819*a* and 819*b* are drilled sufficiently deeply that a cut is made into the material of the outer electrode 803, thereby forming a pair of sharp edged openings in the outer electrode 803 that serve as the ion inlets 805*a* and 805*b*.

Figure 8C:
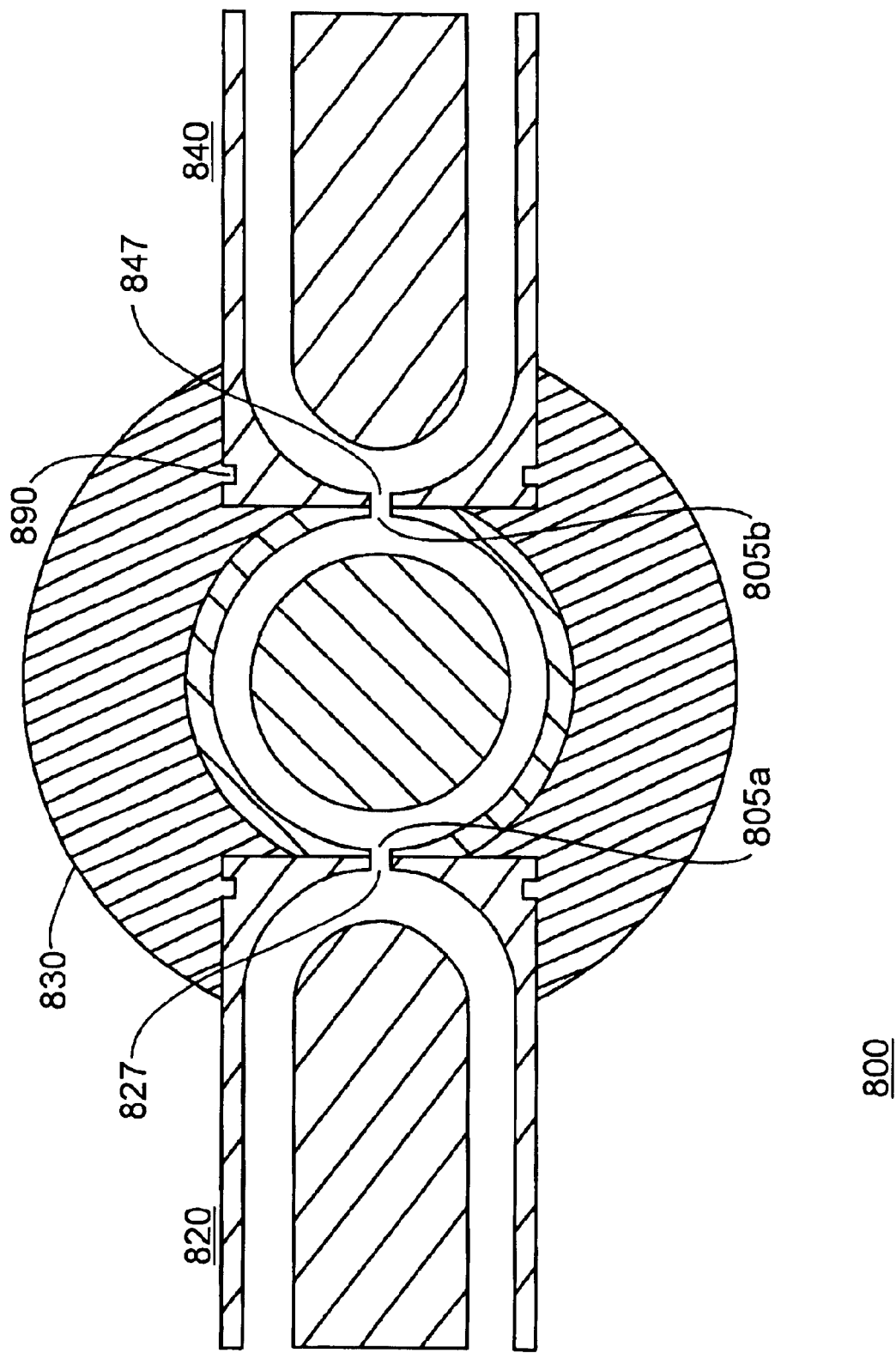
FIG. 8c shows is a simplified cross sectional view of the multiple FAIMS device of FIG. 8a, and illustrating the manner in which the two trapping FAIMS devices are mounted relative to the other FAIMS device.

Referring to FIG. 8*c*, shown is a simplified cross sectional view of multiple FAIMS device 800, illustrating how the tFAIMS 820 and tFAIMS 840 are inserted into the supporting sleeve 830. By placing a small O-ring in an O-ring groove on the outer surface of the outer electrode of each tFAIMS device, a gas tight connection between each tFAIMS and the FAIMS 880 is established while maintaining electrical isolation. If an inlet into FAIMS 880 is in the form of a slit, the O-ring groove is located in position 890. In this case, separate means (not shown) for insulating the FAIMS devices 820 and 840 from FAIMS 880 may be required.

Figure 9A:
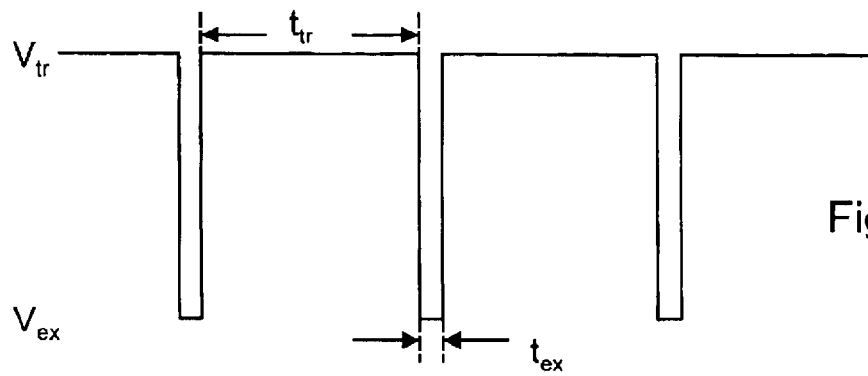
Figure 9B:
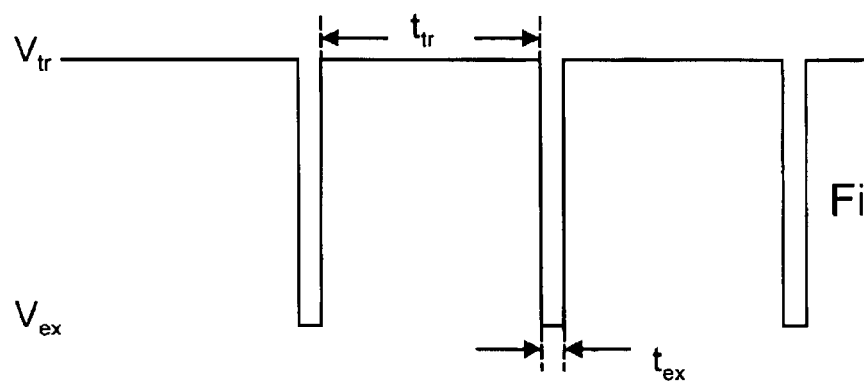
Figure 9C:
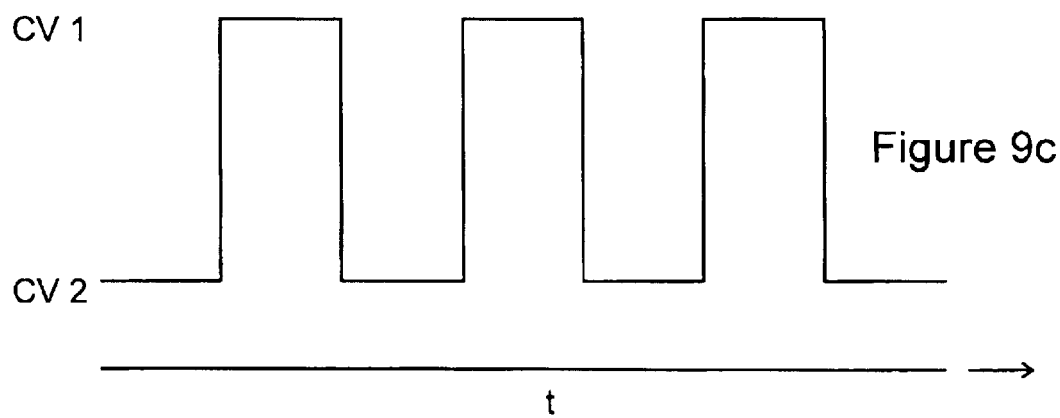

Referring now to FIGS. 9*a* through 9*c*, shown are time-potential profiles used in the operation of the multiple FAIMS device 800. Relevant times are ion injection time $t_{tr}$ during which ions are trapped in a tFAIMS, and ion extraction time $t_{ex}$, during which ions are extracted from a tFAIMS. Referring to FIG. 9*a*, shown is a time-profile of the $V_{tF1}$ voltage applied to the inner electrode 821 of tFAIMS 820. A short period in time $t_{ex}$, during which an extraction voltage $V_{ex}$ is applied to the inner electrode 821, is followed by a longer period in time $t_{tr}$, during which a trapping voltage $V_{tr}$ is applied to the inner electrode 821. Referring to FIG. 9*b*, shown is a time-profile of the $V_{tF2}$ voltage applied to the inner electrode 841 of tFAIMS 840. The extraction pulses applied to tFAIMS 840 are offset in time compared to the extraction pulses applied to tFAIMS 820. Referring to FIG. 9*c*, shown is a time-profile for the CV applied to the inner electrode 801 of FAIMS 880. A different voltage is applied for transmission of ions from FAIMS 820 than is applied for transmission of ions from FAIMS 840, referred to as CV1 and CV2, respectively. Optionally, if a same ion of interest from tFAIMS 820 and tFAIMS 840 is desired, the CV of FAIMS 880 is not changed. Not shown in FIGS. 9*a* through 9*c* are the asymmetric waveform voltages (DV) applied to the inner electrodes of the three FAIMS. The polarity and the magnitude of pulses shown in FIGS. 9*a* through 9*c* are only illustrative of the timing, and the voltage and polarity of the pulses will depend on the experimental parameters including, but not limited to, the polarity of the charge on the ion of interest, the electrode to which the voltage is applied, the type of ion response to strong electric fields, gas temperature, gas pressure, and other appropriate parameters. The asymmetric waveforms applied to tFAIMS 820 and 840, and to FAIMS 880, are not necessarily identical, but it is understood that electrical parameters are selected that are suitable for the transmission of ions of interest. Optionally, the outer electrodes of tFAIMS 820 and 840, and of FAIMS 880 are held at a same applied dc voltage.

The multiple FAIMS device 800 is capable of collecting data from two independent ion streams flowing from ionization sources tFAIMS 820 and tFAIMS 840 into ion inlets 805*a* and 805*b*, respectively, of FAIMS 880. During the portion of the cycle, in which ions are extracted from ionization source tFAIMS 820 and are passing through FAIMS 880, a second stream of ions is being readied by trapping within ionization source tFAIMS 840. During the second portion of a cycle, ions are extracted from tFAIMS 840 and are passing through FAIMS 880 while a new stream of ions is being readied by trapping in tFAIMS 820. In this mode of operation the analyzing device coupled to the ion outlet 807, such as a mass spectrometer, is being used effectively. A person of skill in the art will recognize that the principles illustrated for two ionization sources are readily extended to apply to more than two ionization sources.

The embodiment disclosed in FIG. 8*a* is optionally modified to decrease ion loss for some applications. For example, when either the inner electrode 841 or the outer electrode 843 of tFAIMS 840 is pulsed to extract ions into FAIMS 880, the ions collected in a trapping region 814d at the tip of the inner electrode 841 are pushed by the newly modified electric fields towards the ion outlet 847. The change of the applied voltage also disturbs equilibrium conditions that existed in the analyzer region 814b of FAIMS device 840, and the ions that were stable in the analyzer region 814b are lost to the walls. Depending on variables such as gas flow rate through tFAIMS 840 and length of the analyzer region, there will be a finite amount of time, for example, 50 to 100 ms, during which ions make their way from ion inlet 845, along the analyzer region 814b, and to the trapping region 814d of tFAIMS 840. A short path length from the ion inlet 845 to the trapping region of tFAIMS 840 will reduce ion loss and the "dead time" before ions begin to accumulate under the equilibrium conditions.

Figure 10B:
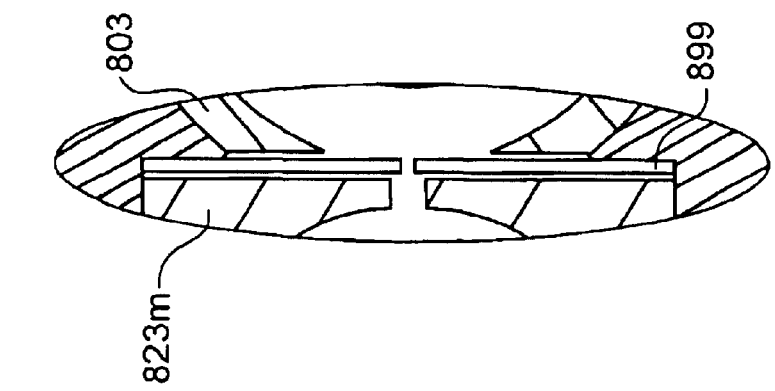
FIG. 10b shows an enlarged partial view of the multiple FAIMS device of FIG. 10a about a region proximate the disk electrode.
Figure 10A:
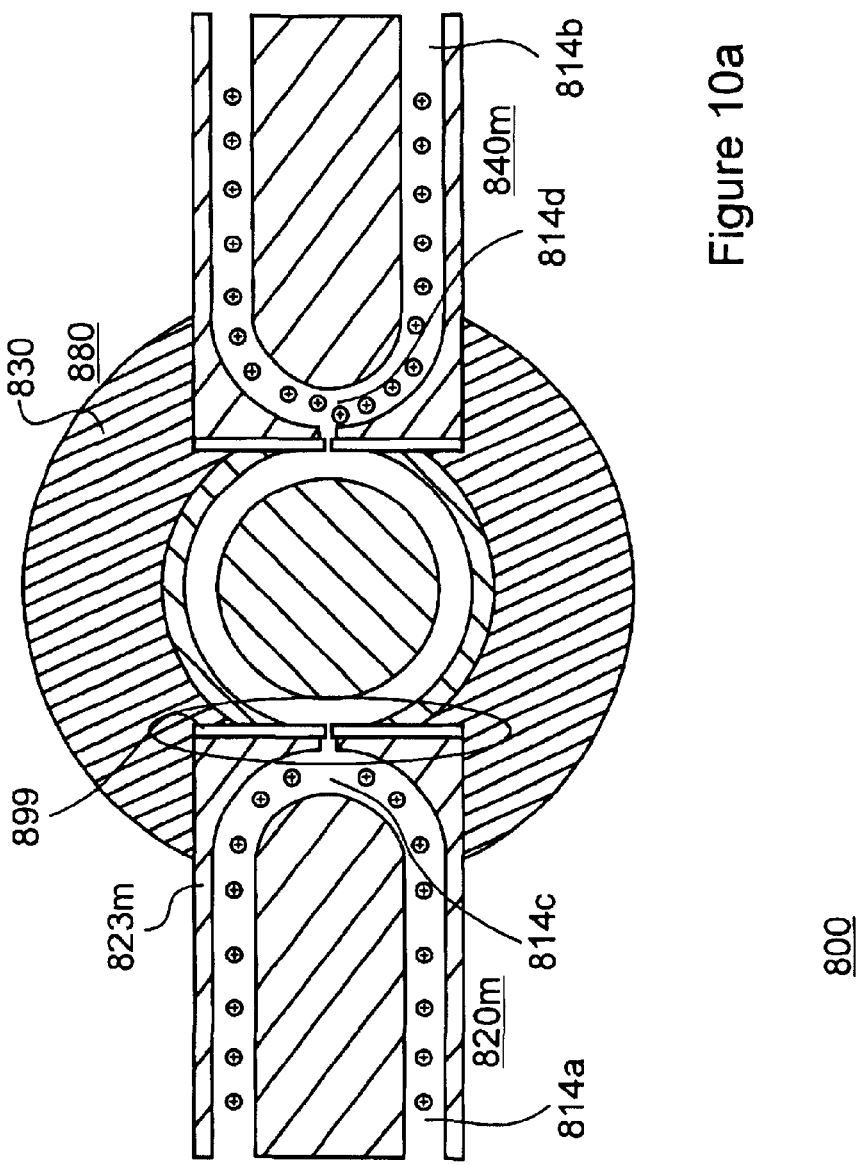
FIG. 10a shows a simplified cross sectional view of another multiple FAIMS device, including two trapping FAIMS devices that are aligned one each with ion inlets into another FAIMS device, each trapping FAIMS device including a modified outer electrode and an electrically isolated disk electrode.

One option for further improving the efficiency of a multiple FAIMS device through the elimination of the "dead time" is to provide a disc electrode intermediate the ion outlet of a first FAIMS analyzer and the ion inlet of a second FAIMS analyzer. Referring now to FIG. 10a, shown is a simplified cross sectional view of a multiple FAIMS device according to the instant invention, in which the outer electrode 823 of FAIMS 820 is segmented into two electrically isolated segments, modified outer electrode 823m and a disk electrode 899. The analyzer region of the tFAIMS 820m is formed by the segmented outer electrode that has been divided into separate mechanically and electrically isolated components. If the two segments 823m and 899 of the outer electrode are connected electrically, or if a same voltage is applied to each segment, then the two segments 823m and 899 behave substantially as a single, non-segmented outer electrode. Referring now to FIG. 10b, which is an enlarged view of the segmented outer electrode of tFAIMS 820m, disc electrode 899 has a smaller opening than outer electrode 823m. Thus, when voltages are applied to the disc electrode 899, that differ from voltages applied to the outer electrode 823m, the disk electrode 899 modifies trapping fields in tFAIMS 820m. The ions are ejected from the trapping region 814c of tFAIMS 820m by stepwise changing the voltage applied to disc electrode 899. The advantage of this approach is that the portion of the analyzer region of FAIMS 820m that is disturbed by changes in electric fields is limited to the immediate vicinity of disc electrode 899. Electric fields present elsewhere in the analyzer region 814a are not substantially disturbed so that ions being carried by a gas flow along through the analyzer region 814a are not lost during application of an extraction pulse to the disc electrode 899. The extraction pulse removes only the ions in the trapping region, thereby causing minimal dead time between the extraction of one set of trapped ions and the onset of trapping of newly arriving ions.

Of course, at the time during which ions are being extracted from the trapping region 814c of FAIMS 820m, ions transmitted through the analyzer region 814b of FAIMS 840m are optionally being accumulated in the trapping region 814d. This is the operating condition illustrated at FIG. 10a. The alternating accumulation, or trapping, and extraction of ions from FAIMS 820m and FAIMS 840m is a very efficient operating mode for delivering ions from two independent ionization sources to a single detector or analyzer, for example a not shown mass spectrometer coupled to the ion outlet of FAIMS 880.

Further advantages associated with multiple FAIMS device 800 include the use of different carries gases in tFAIMS 820 and 840, as well as different operating temperatures. Also, irradiation sources possibly introduced at the interface between tFAIMS 820 or 840 and FAIMS 880 hold a potential to further manipulate the ion characteristics of ions introduced into FAIMS 880.

Figure 11:
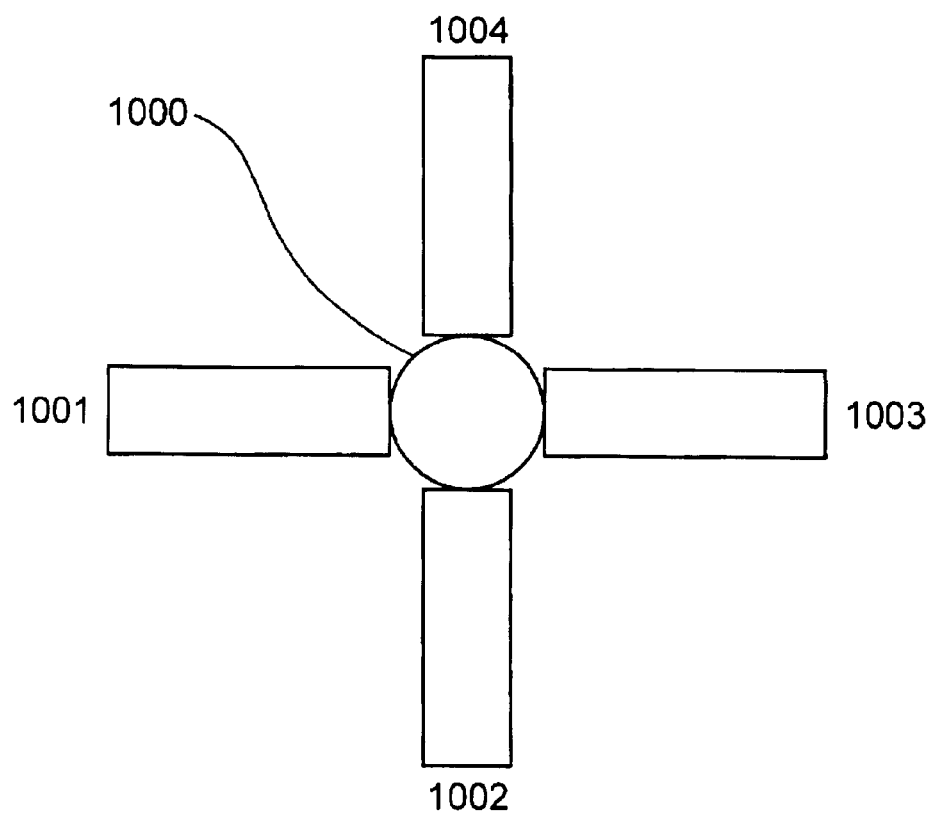
FIG. 11 shows a simplified block diagram of another multiple FAIMS device having four tFAIMS devices.
Figure 12:
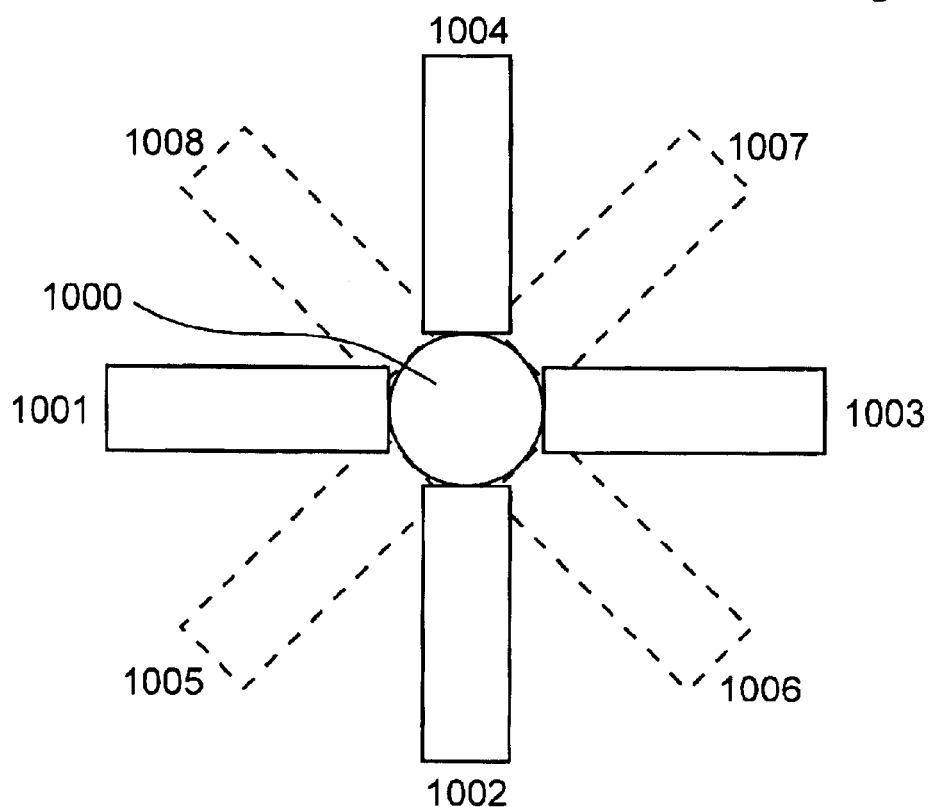
FIG. 12 shows a simplified block diagram of a multiple FAIMS device having eight tFAIMS devices.

The embodiments for a multiple FAIMS are not restricted to include two tFAIMS only. Referring now to FIG. 11, shown is a schematic view of a multiple FAIMS device, combining a FAIMS analyzer 1000 having multiple ion inlets coupled with four tFAIMS devices 1001, 1002, 1003, and 1004. In FIG. 12, shown is a schematic view of a multiple FAIMS device, combining a FAIMS analyzer 1000 having multiple ion inlets coupled with eight tFAIMS devices 1001–1008.

The number of tFAIMS devices combined with a single FAIMS operating in continuous mode is limited. Besides size constraints that physically restrict the number of tFAIMS devices mounted to the exterior of a multiple inlet FAIMS analyzer, there is also the issue of the time required for the ions to travel from a tFAIMS, through a continuous flow FAIMS wherein the multiple FAIMS device is coupled to an analyzer such as a mass spectrometer. Since the gas flow rate through the continuous flow FAIMS is controlled by the flow rate $R_m$ into the mass spectrometer, the gas flow rate through each of n tFAIMS devices is approximately $R_m/n$. At non-optimal flow rates, ion losses in each of the n tFAIMS devices increase. The problem is circumvented by allowing a portion of the carrier gas or gases to exit the continuous flow FAIMS or any of the tFAIMS other than through an ion outlet in communication with the analyzing device.

Figure 13:
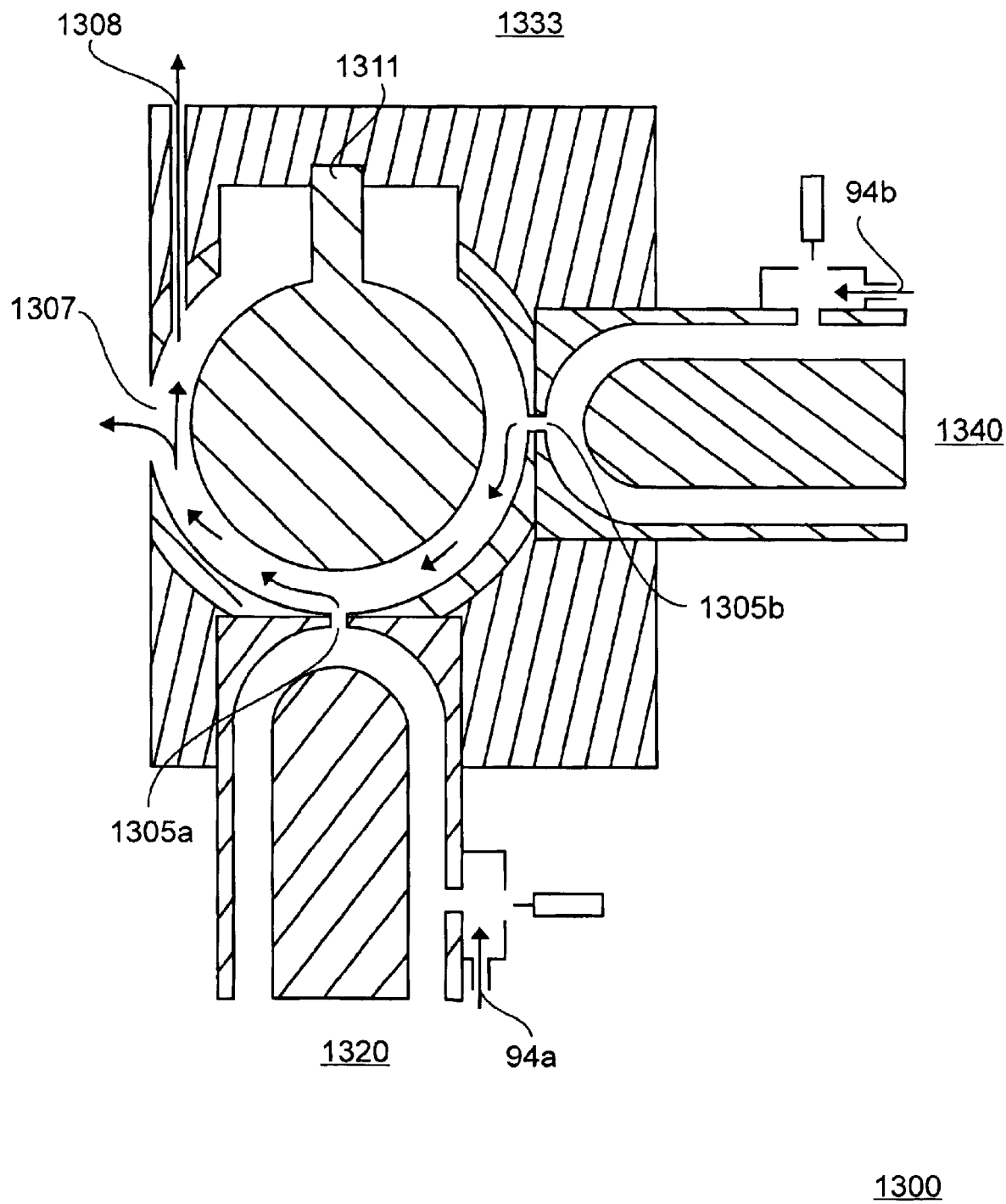
FIG. 13 shows a cross sectional side view of yet another multiple FAIMS device.

Referring now to FIG. 13, shown is a cross sectional side view of a multiple FAIMS device according to the instant invention. The multiple FAIMS device 1300 includes two trapping tFAIMS devices 1320 and 1340 attached to one side-to-side FAIMS device sFAIMS 1333. sFAIMS 1333 comprises a barrier in the form of a protrusion 1311 so that gas flows only in one direction through sFAIMS 1333, illustrated in FIG. 13 by a series of closed-headed arrows. A gas outlet 1308 is disposed near an ion outlet 1307, so that gas near the ion outlet 1307 splits into a flow exiting through the ion outlet 1307 and a flow exiting through the gas outlet 1308. Rates of curtain gas flows 94a and 94b into each of the tFAIMS devices 1320 and 1340 are important variables, since ions extracted into sFAIMS 1333 have different path lengths to the ion outlet 1307, depending on whether the ions enter at ion inlet 1305a or ion inlet 1305b. For example, if curtain gas flow 94a is significantly higher than curtain gas flow 94b, then all of a gas flow through the ion outlet 1307 originates from the gas flow through ion inlet 1305a. In this instance, the gas flow between ion inlet 1305a and ion inlet 1305b, as well as through ion inlet 1305b, is possibly reversed in direction, making it other than possible to transport ions from ion inlet 1305b to the ion outlet 1307.

The embodiments previously discussed using tandem FAIMS devices provide a means for efficiently sampling ions of interest, making improved detection possible. In the embodiments which follow, multiple ion inlets are advantageously provided for introducing ions produced at a single ion source into a FAIMS analyzer region. For instance, several types of atmospheric pressure ionization sources produce a wide ion dispersion plume. Accordingly, when using an electrospray ionization source, for example, ions and charged droplets travel along an electric field gradient in a direction away from a tip of a needle and towards a counter electrode. Unfortunately, a diverging cloud of ions is not efficiently sampled by a single small opening of the type that is commonly provided within the counter electrode of a prior art FAIMS device. A simple solution to this problem would seem to include providing a larger opening for sampling the ion plume from the ionization source. In fact, as the opening size is increased, some improvement is observed. However, in an experiment with singly charged ions of leucine enkephalin, when a 2 mm opening is compared to a 1 mm opening, only a 35% increase in absolute signal intensity is observed, compared to a 300% increase in the area of the opening. It is likely that the signal intensity does not increase in proportion to the increase to the area of the opening because the resulting changes to gas flows and electric fields in the region near an ion inlet affect the efficiency of transfer of ions into a FAIMS analyzer region. For example, a strong electric field between the inner and outer electrode of a FAIMS device that is necessary for its operation decreases significantly if there is a discontinuity in either the inner or outer electrodes, such as a hole in the outer electrode. If the hole is small, and if its diameter is less than a spacing between inner and outer electrodes, electric fields in the region between the hole and the inner electrode remain similar to fields elsewhere between the inner and outer electrode. However, if the hole is large, its diameter being for example twice the spacing between the inner and outer electrodes, electric fields decrease in strength between the hole and the inner electrode. Ions, which would otherwise have been focused under the operating conditions of CV and DV, will hit one of the inner and outer electrodes and be lost. Therefore, further increases in size of an ion inlet are not expected to give significantly improved results.

Figure 14A:
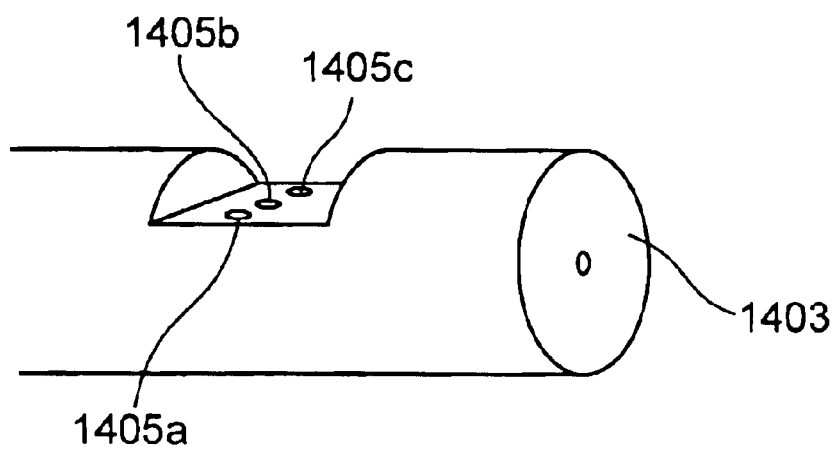
FIG. 14a shows a schematic view of a FAIMS outer electrode having a first ion inlet grouping.
Figure 14B:
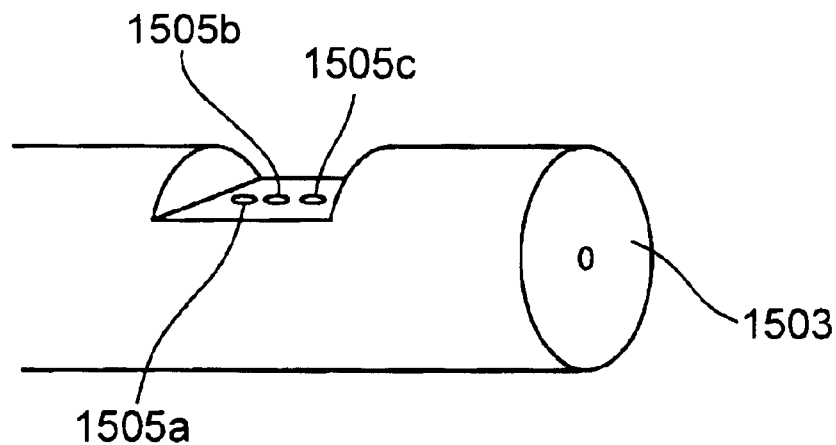
FIG. 14b shows a schematic view of a FAIMS outer electrode having a second ion inlet grouping; and, FIG. 14c shows a schematic view of a FAIMS outer electrode having a third ion inlet grouping.
Figure 14C:
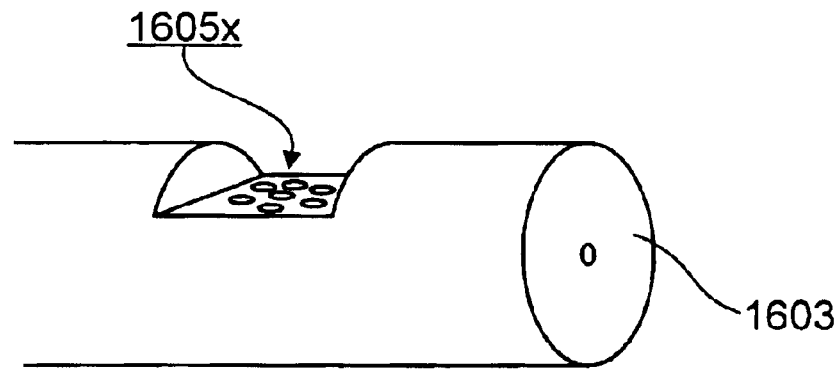

Increased sample introduction is achieved by providing several openings in the outer electrode of a FAIMS device, such as is illustrated at FIGS. 14a–c. The multiple ion inlet groupings that are shown at FIGS. 14a–c result in a significant improvement in the observed signal intensity relative to a device with a single small opening. In FAIMS devices having a separate desolvation chamber, a counter electrode or curtain plate is located in front of the ion inlet. Therefore, provision is made for the curtain plate to have openings of at least the same size, and in the same position, as the openings in the ion inlet groupings of the outer electrode. Preferably, the openings in the curtain plate are somewhat larger to allow for maximal ion transmission through the curtain plate, while at the same time satisfying the condition of an area of holes that does not become so large as to prevent efficient desolvation. If the holes are large, the gas flow velocity is not constant across the diameter of the hole. If there are several such holes, flow through one hole may exceed flow though other holes, and if flow velocity or flow volume is decreased, an inefficient desolvation of ions may result. Poor desolvation reduces an effectiveness of ion separation in the analyzer region of a FAIMS device, and if neutral solvent vapours contaminate gas flowing into a FAIMS analyzer, the FAIMS device is likely to fail. For the use of several ion inlets, a reduction in the size of each ion inlet is advisable to allow for efficient desolvation. In FAIMS devices not having a separate desolvation chamber, the ion inlets are of a suitable size for maintaining sufficient velocity of gas flowing out of the analyzer region through the ion inlets for desolvation to occur. Numerous configurations of multiple ion inlet groupings are possible and the ion inlet groupings shown at FIG. 14 should not be considered an exclusive list of possible configurations. In addition, as long as the total area of the ion inlet does not become too large for ion desolvation, the ion inlet size is not restricted to a particular dimension, nor does the size of each ion inlet need to be kept equal. The location of an ion inlet grouping or of multiple ion inlet groupings on an outer electrode is variable. With a domed FAIMS device, ion inlets are to be placed at any location around the circumference of the outer electrode at a same distance from an ion outlet. A location of an ion inlet is also adjustable along a length of an outer electrode. Moving the ion inlet farther away from the an ion outlet increases ion transit time, possibly causing a reduction in signal intensity due to loss mechanisms such as diffusion and space charge repulsion. Moving the ion inlet closer toward an ion outlet possibly improves sensitivity due to reduced ion transit time. However, if the ion inlet is placed too close to the ion outlet, insufficient time for ion separation results in a reduction of peak separation capabilities of a FAIMS device.

Referring specifically to FIG. 14a, shown is a schematic view of a FAIMS outer electrode having a first ion inlet grouping according to the instant invention. A FAIMS device comprises an outer electrode 1403 having a length. In the outer electrode 1403, disposed are three circular ion inlets 1405a–c, the ion inlets 1405a–c positioned on a line substantially perpendicular to the length of the outer electrode.

Referring specifically to FIG. 14b, shown is a schematic view of a FAIMS outer electrode having a second ion inlet grouping according to the instant invention. A FAIMS device comprises an outer electrode 1503 having a length. In the outer electrode 1503, disposed are three circular ion inlets 1505a–c, the ion inlets 1505a–c positioned on a line substantially parallel to the length of the outer electrode.

Referring specifically to FIG. 14c, shown is a schematic view of a FAIMS outer electrode having a third ion inlet grouping according to the instant invention. A FAIMS device comprises an outer electrode 1603 having a length. In the outer electrode 1603, disposed is a plurality of essentially circular ion inlets, shown generally at 1605x, the plurality of ion inlets 1605x positioned so as to adopt a two-dimensional closest packing of circles.

Numerous other embodiments may be envisaged without departing from the spirit and scope of the invention.

What is claimed is:

1. An apparatus for separating ions in the gas phase, comprising:
    a high field asymmetric waveform ion mobility spectrometer including an inner electrode having an outer surface and a length; and,
    an outer electrode having an inner surface and a length and surrounding the inner electrode over at least a portion of the length of the inner electrode, the inner electrode and the outer electrode defining an analyzer region therebetween and being disposed in a spaced apart arrangement for allowing ions to propagate therebetween, the outer electrode comprising an outlet from the analyzer region and at least a first ion inlet and a second distinct ion inlet into the analyzer region, the first ion inlet and the second distinct ion inlet each for communicating with at least one ionization source, the inner electrode and the outer electrode for providing an electric field within the analyzer region resulting from application of an asymmetric waveform voltage to at least one of the inner electrode and the outer electrode and from application of a compensation voltage to at least one of the inner electrode and outer electrode, the electric field for selectively transmitting ions within the analyzer region between at least one of the first ion inlet and the second distinct ion inlet and the outlet.

2. An apparatus according to claim 1, comprising at least one ionization source in communication with the first ion inlet and with the second distinct ion inlet.

3. An apparatus according to claim 1, comprising a first ionization source in communication with the first ion inlet and a second ionization source in communication with the second distinct ion inlet, the second ionization source separate from the first ionization source.

4. An apparatus according to claim 1, wherein the first ion inlet is disposed within a portion along the inner circumference of the outer electrode and the second distinct ion inlet is disposed approximately opposite to the portion, and wherein the outlet is positioned approximately intermediate the first ion inlet and the second distinct ion inlet.

5. An apparatus according to claim 4, comprising a first ionization source in communication with the first ion inlet and a second ionization source in communication with the second distinct ion inlet, the second ionization source separate from the first ionization source.

6. An apparatus according to claim 1, comprising a gas inlet disposed within the outer electrode and positioned such that a portion of a flow of gas through the analyzer region between the gas inlet and the outlet flows adjacent to the first ion inlet and the second distinct ion inlet.

7. An apparatus according to claim 1, comprising a gas inlet disposed in the outer electrode at a position that is approximately intermediate the first ion inlet and the second distinct ion inlet.

8. An apparatus according to claim 7, comprising a first ionization source in communication with the first ion inlet and a second ionization source in communication with the second distinct ion inlet, the second ionization source separate from the first ionization source.

9. An apparatus according to claim 8, wherein the first ion inlet, the second distinct ion inlet, and the gas inlet are positioned adjacent one to another along the inner circumference of the outer electrode.

10. An apparatus according to claim 8, wherein the first ion inlet, the second distinct ion inlet, and the gas inlet are positioned adjacent one to another along the length of the outer electrode.

11. An apparatus according to claim 1, comprising a barrier extending between the inner electrode and the outer electrode, the barrier disposed intermediate the first ion inlet and the second distinct ion inlet, the barrier for directing a flow of a gas entering the analyzer region through one of the first ion inlet and the second distinct ion inlet in one direction around the outer circumference of the inner electrode and toward the outlet.

12. An apparatus according to claim 1, comprising an ionization source selecting electrode having an inner circumference and a length and being generally coaxially aligned adjacent to an outer circumference of the outer electrode, the ionization source selecting electrode having an inlet therethrough and being moveable between first and second positions, the inlet for being aligned with the first ion inlet for supporting ion flow therethrough and for substantially preventing ion flow through the second distinct ion inlet when the ionization source selecting electrode is in the first position and for being aligned with the second distinct ion inlet for supporting ion flow therethrough and for substantially preventing ion flow through the first ion inlet when the ionization source selecting electrode is in the second position.

13. An apparatus according to claim 12, comprising a first ionization source in communication with the first ion inlet and a second ionization source in communication with the second distinct ion inlet, the second ionization source separate from the first ionization source.

14. An apparatus according to claim 12, wherein the ionization source selecting electrode is rotatably coupled to the outer electrode.

15. An apparatus according to claim 14, comprising a guide member disposed along a surface of at least one of the ionization source selecting electrode and the outer electrode, for minimizing movement of the ionization source selecting electrode in a direction along the length of the outer electrode.

16. An apparatus according to claim 14, wherein the ionization source selecting electrode comprises at least a plug disposed along the inner circumference of the ionization source selecting electrode at a point relative to the inlet such that when the inlet is aligned with one of the first ion inlet and the second distinct ion inlet, the at least a plug forms approximately a seal against the other one of the first ion inlet and the second distinct ion inlet.

17. An apparatus according to claim 12, wherein the ionization source selecting electrode includes an outer surface that is fabricated from an electrically conductive material.

18. An apparatus according to claim 17, wherein the ionization source selecting electrode is made from an electrically conductive material.

19. An apparatus according to claim 3, wherein at least one of the first ionization source and the second ionization source comprises a second high field asymmetric waveform ion mobility spectrometer having an outlet from an analyzer region thereof that is generally aligned with a corresponding one of the first ion inlet and the second distinct ion inlet.

20. An apparatus according to claim 19, comprising a device for producing ions from a sample medium, the device for producing ions being in fluid communication with the second high field asymmetric waveform ion mobility spectrometer for providing ions thereto, at least some of the ions for being transmitted through the second high field asymmetric waveform ion mobility spectrometer for introduction through the corresponding one of the first ion inlet and the second distinct ion inlet.

21. An apparatus according to claim 19, comprising a disk electrode disposed between the outlet of the second high field asymmetric waveform ion mobility spectrometer and the corresponding one of the first ion inlet and the second distinct ion inlet, for modifying an electric field within the analyzer region of the second high field asymmetric waveform ion mobility spectrometer.

22. An apparatus according to claim 19, wherein the second high field asymmetric waveform ion mobility spectrometer is a trapping FAIMS.

23. An apparatus according to claim 22, comprising a disk electrode disposed between the outlet of the second high field asymmetric waveform ion mobility spectrometer and the corresponding one of the first ion inlet and the second distinct ion inlet, for modifying an electric field within the analyzer region of the second high field asymmetric waveform ion mobility spectrometer.

24. An apparatus according to claim 1, comprising a first other high field asymmetric waveform ion mobility spectrometer in fluid communication with the first ion inlet for providing ions therethrough and a second other high field asymmetric waveform ion mobility spectrometer in fluid communication with the second distinct ion inlet for providing ions therethrough, each one of the first other high field asymmetric waveform ion mobility spectrometer and the second other high field asymmetric waveform ion mobility spectrometer comprising first and second spaced apart electrodes defining an analyzer region therebetween.

25. An apparatus according to claim 24, comprising a disk electrode disposed between at least one of an outlet of the first other high field asymmetric waveform ion mobility spectrometer and the first ion inlet and an outlet of the second other high field asymmetric waveform ion mobility spectrometer and the second distinct ion inlet, for modifying an electric field within the analyzer region of the at least one of the first other high field asymmetric waveform ion mobility spectrometer and the second other high field asymmetric waveform ion mobility spectrometer.

26. An apparatus according to claim 25, wherein the disk electrode is a solid disk of an electrically conductive material comprising an orifice for allowing ions to propagate therethrough.

27. An apparatus according to claim 24, comprising a barrier extending between the inner electrode and the outer electrode, the barrier disposed intermediate the second distinct ion inlet and the outlet, the barrier for directing a flow of a gas entering the analyzer region through the distinct second ion inlet in one direction around the outer circumference of the inner electrode and toward the outlet.

28. An apparatus according to claim 24, comprising a barrier extending between the inner electrode and the outer electrode, the barrier disposed intermediate the first ion inlet and the second distinct ion inlet, the barrier for directing a flow of a gas entering the analyzer region through one of the first ion inlet and the second distinct ion inlet in one direction around the outer circumference of the inner electrode and toward the outlet.

29. An apparatus according to claim 24, comprising:
  disposed in the outer electrode, an additional gas outlet in vicinity to the ion outlet for allowing gas entering the analyzer region through an ion inlet and traveling toward the ion outlet to exit the analyzer region.

30. An apparatus according to claim 1, wherein the first ion inlet and the second distinct ion inlet are disposed adjacent to a same ionization source, such that the first ion inlet and the second distinct ion inlet are in fluid communication with the same ionization source.

31. An apparatus according to claim 30, comprising a plurality of ion inlets within the outer electrode, the plurality of ion inlets including the first ion inlet and the second distinct ion inlet.

32. An apparatus according to claim 30, wherein the first ion inlet and the second distinct ion inlet define a line substantially perpendicular to the length of the outer electrode.

33. An apparatus according to claim 30, wherein the first ion inlet and the second distinct ion inlet define a line substantially parallel to the length of the outer electrode.

34. An apparatus according to claim 31, wherein the plurality of ion inlets is arranged in a pattern resembling a two-dimensional closest packing.

35. A method for separating ions originating from different ionization sources, the method comprising the steps of:

providing a high field asymmetric waveform ion mobility spectrometer having at least a first ion inlet and a second distinct ion inlet into an analyzer region thereof, the first ion inlet and the second distinct ion inlet being separately in fluid communication with a first ionization source and a second ionization source, respectively;

directing ions from at least one of the first ionization source and the second ionization source toward the first ion inlet and the second distinct ion inlet, respectively;

receiving ions including ions of interest into the analyzer region via at least one of the first ion inlet and the second ion inlet; and, transmitting the ions of interest through the analyzer region between the at least one of the first ion inlet and the second distinct ion inlet and an outlet of the analyzer region.

36. A method according to claim 35, wherein at a given time ions are selectively introduced into the analyzer region through one of the first ion inlet and the second distinct ion inlet.

37. A method according to claim 35, comprising a step of selectively switching between receiving ions into the analyzer region via the first ion inlet and receiving ions into the analyzer region via the second distinct ion inlet.

38. A method according to claim 37, wherein over a period of time different ion inlets are selected as ion inlets for introducing ions into the analyzer region.

39. A method according to claim 37, wherein a selection of an ion inlet is performed by a step of adjusting an ionization source selecting electrode.

40. A method according to claim 36, wherein at least one of the first ionization source and the second ionization source is used in an ion trapping mode of operation.

41. A method according to claim 39, comprising the step of:
  approximately preventing ions originating at one of the first ionization source and the second ionization source from entering the analyzer region during a same overlapping period of time that ions originating at the other one of the first ionization source and the second ionization source are being introduced into the analyzer region.

42. A method according to claim 35, comprising the step of:
  introducing ions produced at the first ionization source and ions produced at the second ionization source into the analyzer region via the first ion inlet and the second distinct ion inlet, respectively, during a same overlapping period of time.

* * * * *